United States Patent
Munro et al.

(10) Patent No.: US 11,189,195 B2
(45) Date of Patent: Nov. 30, 2021

(54) HYSTEROSCOPY TRAINING AND EVALUATION

(71) Applicant: American Association of Gynecological Laparoscopists, Inc., Cypress, CA (US)

(72) Inventors: Malcolm Munro, Tarzana, CA (US); James Messerschmidt, Prescott Valley, AZ (US); Ted Anderson, Franklin, TN (US); Joseph Hudgens, Madison, MS (US); Dervis Demirtas, Rotterdam (NL)

(73) Assignee: AMERICAN ASSOCIATION OF GYNECOLOGICAL LAPAROSCOPISTS, Inc., Cypress, CA (US)

( * ) Notice: Subject to any disclaimer, the term of this patent is extended or adjusted under 35 U.S.C. 154(b) by 480 days.

(21) Appl. No.: 16/165,054

(22) Filed: Oct. 19, 2018

(65) Prior Publication Data
US 2019/0122582 A1  Apr. 25, 2019

Related U.S. Application Data

(60) Provisional application No. 62/575,289, filed on Oct. 20, 2017.

(51) Int. Cl.
*G09B 23/30* (2006.01)
*G09B 23/28* (2006.01)
(Continued)

(52) U.S. Cl.
CPC ............ *G09B 23/285* (2013.01); *A61B 1/303* (2013.01); *A61B 17/00234* (2013.01);
(Continued)

(58) Field of Classification Search
CPC ................................ G09B 23/28; G09B 23/30
(Continued)

(56) References Cited

U.S. PATENT DOCUMENTS 3,199,225 A  8/1965  Robertson
4,907,973 A * 3/1990  Hon ...................... G09B 23/285
                                                434/262
(Continued)

FOREIGN PATENT DOCUMENTS

CA        2846386 A1    2/2013
SG     2013235G-001    4/2013
(Continued)

OTHER PUBLICATIONS

Limbs & Things Inc., Fundamentals of Laparoscopic Surgery Trainer System & Accessories Product Brochure, V.2 May 2016, 4 pages.
(Continued)

*Primary Examiner* — Kurt Fernstrom
(74) *Attorney, Agent, or Firm* — Merchant & Gould P.C.

(57) ABSTRACT

A system for simulating a hysteroscopy procedure is disclosed. The system includes a base station adapted to communicate with a computer having a display monitor. A training box is connected to the base station, and includes a housing having a chamber positioned therein. The chamber simulates the shape of a uterine cavity and includes an opening for receiving an instrument. The instrument is adapted for insertion into the chamber for performing hysteroscopy evaluation exercises including targeting and polyp removal exercises.

16 Claims, 30 Drawing Sheets

(51) Int. Cl.
*A61B 17/00* (2006.01)
*A61B 1/303* (2006.01)
*G09B 9/00* (2006.01)
*A61B 17/42* (2006.01)
*G06F 3/0482* (2013.01)
*G09B 7/06* (2006.01)
*G06F 3/0481* (2013.01)

(52) U.S. Cl.
CPC ............... *G09B 9/00* (2013.01); *A61B 17/42* (2013.01); *A61B 2017/00199* (2013.01); *A61B 2017/00716* (2013.01); *A61B 2017/4216* (2013.01); *G06F 3/0482* (2013.01); *G06F 3/04817* (2013.01); *G09B 7/06* (2013.01)

(58) Field of Classification Search
USPC ........................................ 434/262, 267, 272
See application file for complete search history.

(56) References Cited

U.S. PATENT DOCUMENTS

| | | | |
|---|---|---|---|
| 5,722,836 A | 3/1998 | Younker | |
| 5,800,179 A * | 9/1998 | Bailey | A61B 34/76 434/262 |
| 5,873,732 A | 2/1999 | Hasson | |
| 6,428,323 B1 * | 8/2002 | Pugh | G09B 23/30 434/262 |
| 6,488,507 B1 * | 12/2002 | Stoloff | G09B 23/28 434/272 |
| 6,659,776 B1 | 12/2003 | Aumann et al. | |
| 7,594,815 B2 * | 9/2009 | Toly | G09B 23/285 434/262 |
| 7,731,500 B2 * | 6/2010 | Feygin | G09B 23/285 434/272 |
| 7,802,990 B2 | 9/2010 | Korndorffer, Jr. | |
| 7,837,473 B2 | 11/2010 | Koh | |
| 7,997,903 B2 | 8/2011 | Hasson et al. | |
| 8,007,281 B2 | 8/2011 | Toly | |
| 8,328,560 B2 | 12/2012 | Niblock et al. | |
| 8,460,002 B2 | 6/2013 | Wang | |
| 8,469,716 B2 | 6/2013 | Fedotov et al. | |
| 8,764,452 B2 | 7/2014 | Pravong et al. | |
| D717,444 S | 11/2014 | Pastrick | |
| 9,123,261 B2 * | 9/2015 | Lowe | G09B 23/288 |
| 9,230,452 B2 * | 1/2016 | Hyltander | G09B 23/28 |
| 9,548,002 B2 | 1/2017 | Black et al. | |
| D794,709 S | 8/2017 | Pastrick | |
| D800,220 S | 10/2017 | Park | |
| 9,842,515 B1 * | 12/2017 | TenBrink | G09B 23/32 |
| 9,959,785 B2 * | 5/2018 | Tortola | G09B 23/285 |
| D819,605 S | 6/2018 | Heath | |
| 10,037,715 B2 * | 7/2018 | Toly | G09B 23/28 |
| D830,557 S | 10/2018 | Sebban | |
| D838,854 S | 1/2019 | Lumme | |
| D844,788 S | 4/2019 | Pastrick | |
| 2004/0142314 A1 | 7/2004 | Hasson | |
| 2004/0175684 A1 | 9/2004 | Kaasa et al. | |
| 2005/0064378 A1 | 3/2005 | Toly | |
| 2005/0084833 A1 * | 4/2005 | Lacey | G09B 23/285 434/262 |
| 2005/0142525 A1 * | 6/2005 | Cotin | G09B 23/285 434/262 |
| 2007/0054254 A1 | 3/2007 | Cook | |
| 2007/0166682 A1 * | 7/2007 | Yarin | G09B 23/285 434/267 |
| 2008/0062299 A1 * | 3/2008 | Matanhelia | G09B 23/285 348/333.11 |
| 2009/0035740 A1 | 2/2009 | Reed | |
| 2010/0291522 A1 | 11/2010 | Cook | |
| 2011/0269109 A2 | 11/2011 | Miyazaki | |
| 2012/0082970 A1 * | 4/2012 | Pravong | G09B 23/30 434/262 |
| 2012/0308977 A1 | 12/2012 | Tortola | |
| 2013/0105346 A1 | 5/2013 | Ramkhelawan et al. | |
| 2014/0051049 A1 | 2/2014 | Jarc et al. | |
| 2014/0087346 A1 | 3/2014 | Breslin et al. | |
| 2014/0220527 A1 | 8/2014 | Li et al. | |
| 2015/0037773 A1 | 2/2015 | Quirarte | |
| 2016/0133158 A1 | 5/2016 | Sui et al. | |
| 2016/0140876 A1 | 5/2016 | Jabbour | |
| 2016/0232819 A1 * | 8/2016 | Hofstetter | G09B 23/28 |
| 2017/0110032 A1 * | 4/2017 | O'Brien | A61B 8/4444 |
| 2017/0148356 A1 * | 5/2017 | Black | G09B 23/285 |
| 2018/0233067 A1 | 8/2018 | Velasco | |
| 2018/0240366 A1 * | 8/2018 | Felsinger | G09B 23/30 |
| 2019/0122582 A1 | 4/2019 | Munro | |

FOREIGN PATENT DOCUMENTS

| | | |
|---|---|---|
| WO | 2007133209 A1 | 11/2007 |
| WO | 2016116567 A1 | 7/2016 |
| WO | 20171735290 A1 | 10/2017 |
| WO | 2018218175 A1 | 11/2018 |

OTHER PUBLICATIONS

Mdedge Obgyn; https://www.mdedge.com/obgyn/article/150339/surgery/2017-update-minimally-invasive-gynecologic-surgery/page/0/1; Nov. 29, 2017; 2017 update on minimally invasive gynecologic surgery.

* cited by examiner

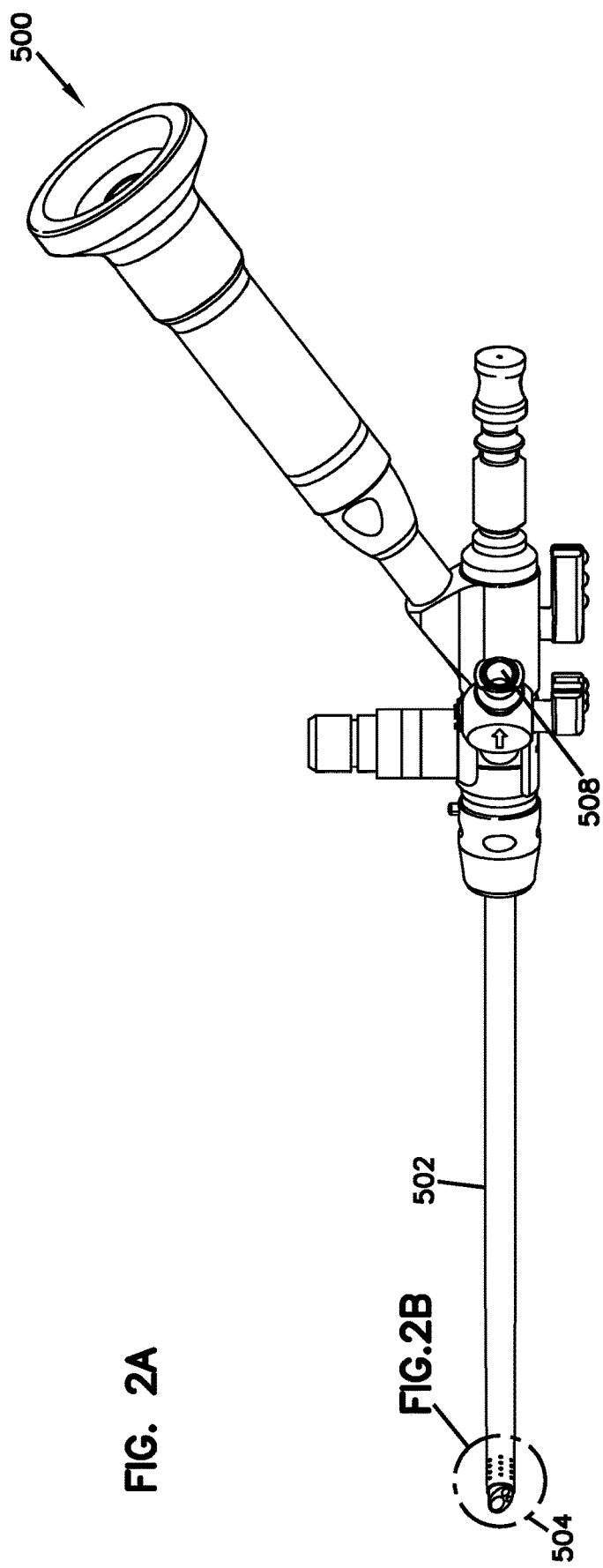
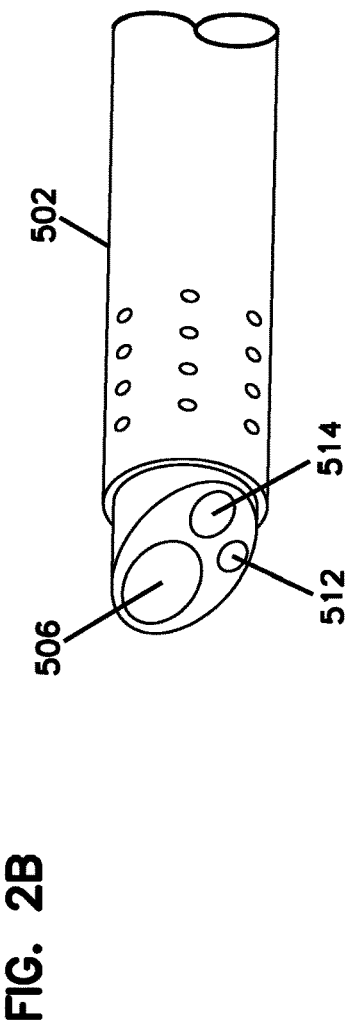
FIG. 2A
FIG. 2B

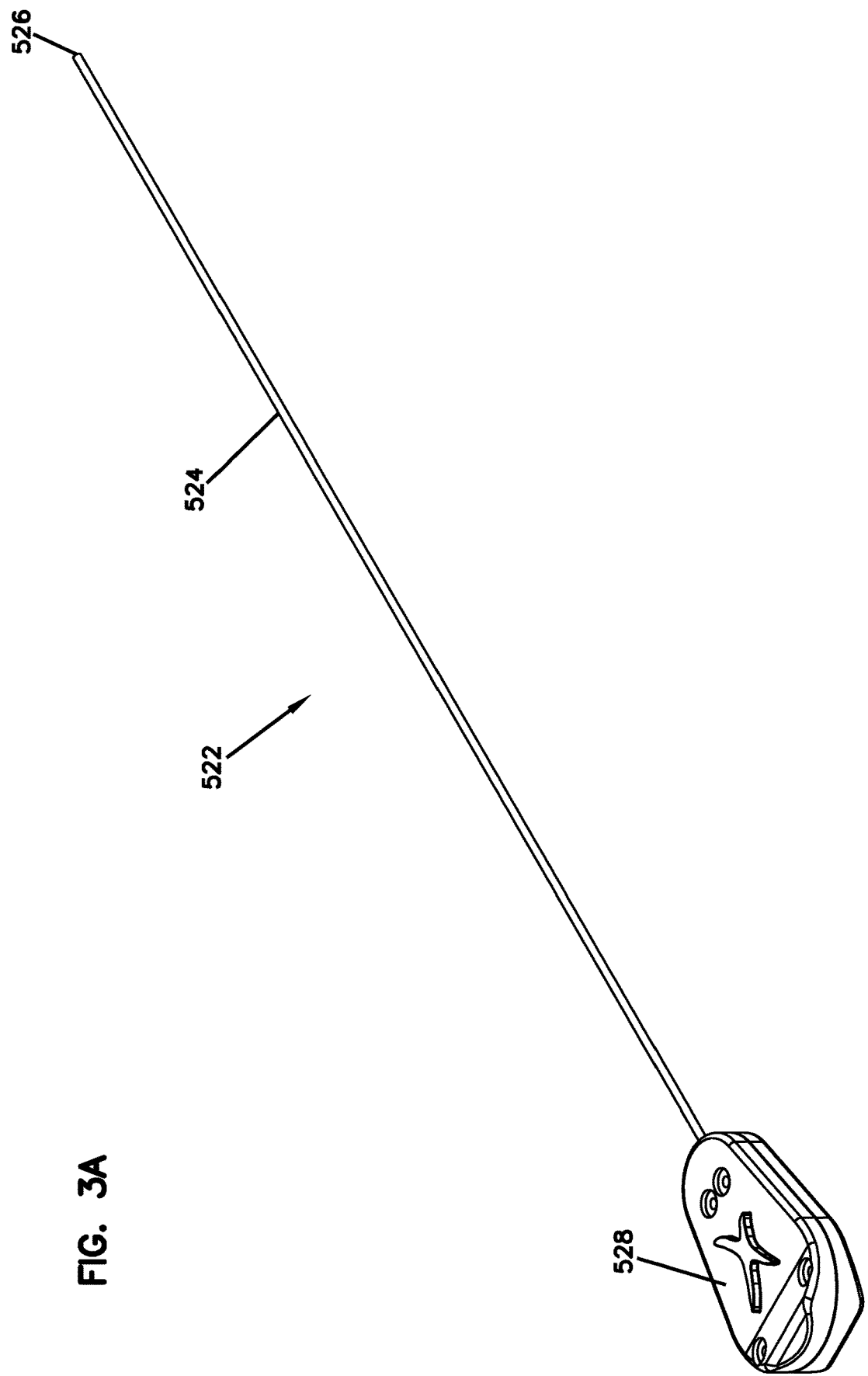

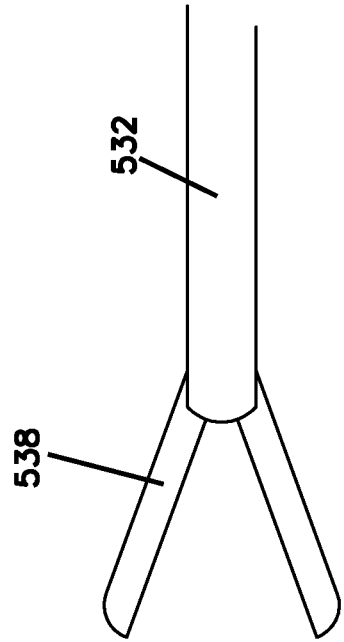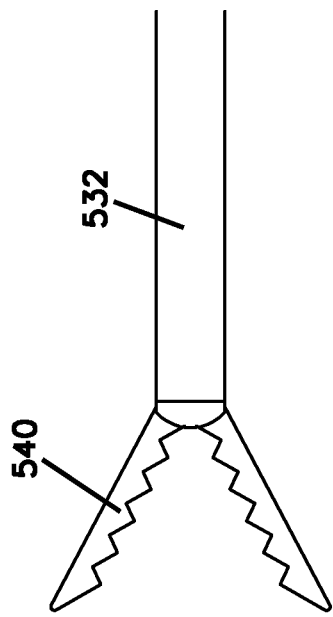
FIG. 4D
FIG. 4E

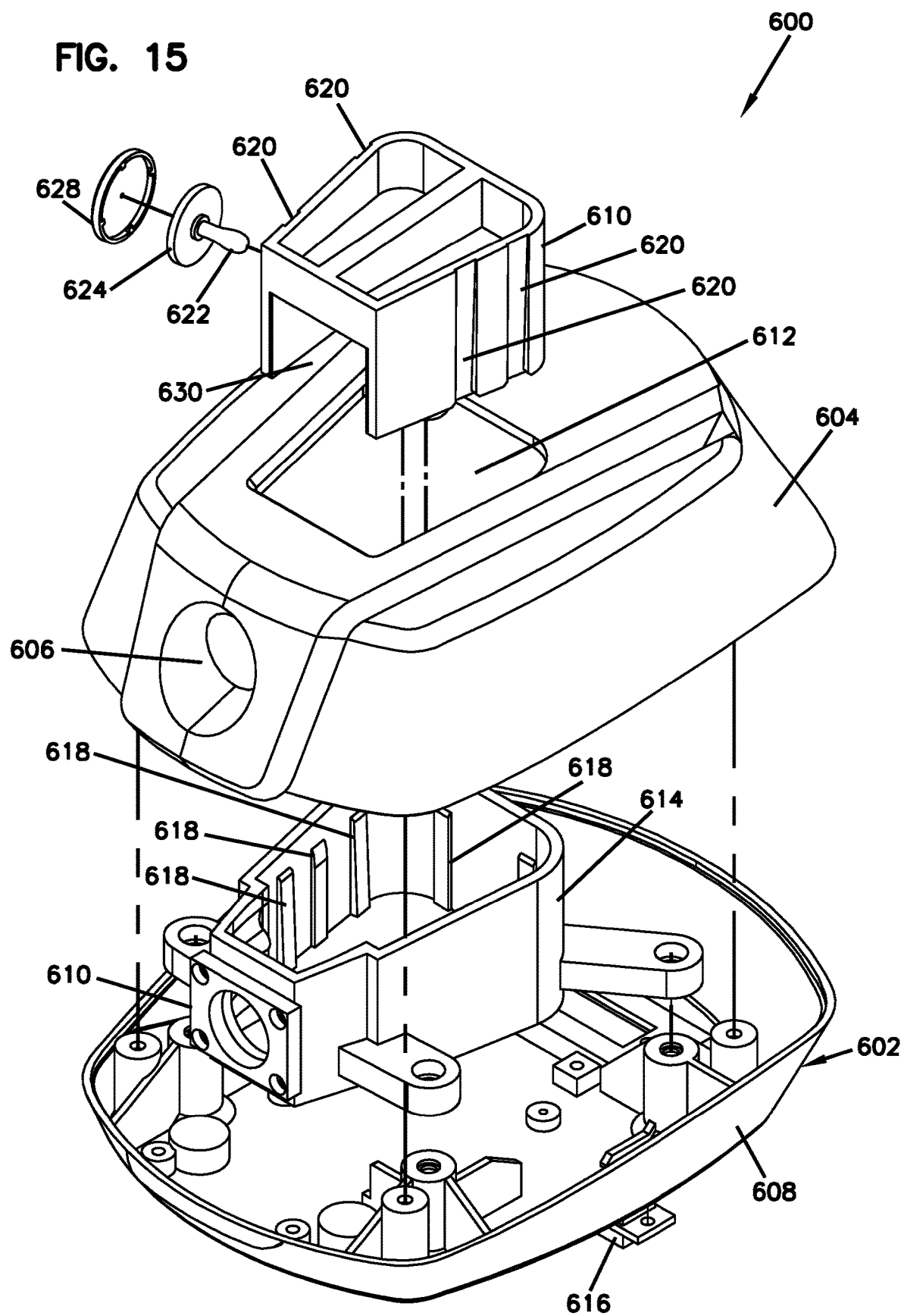

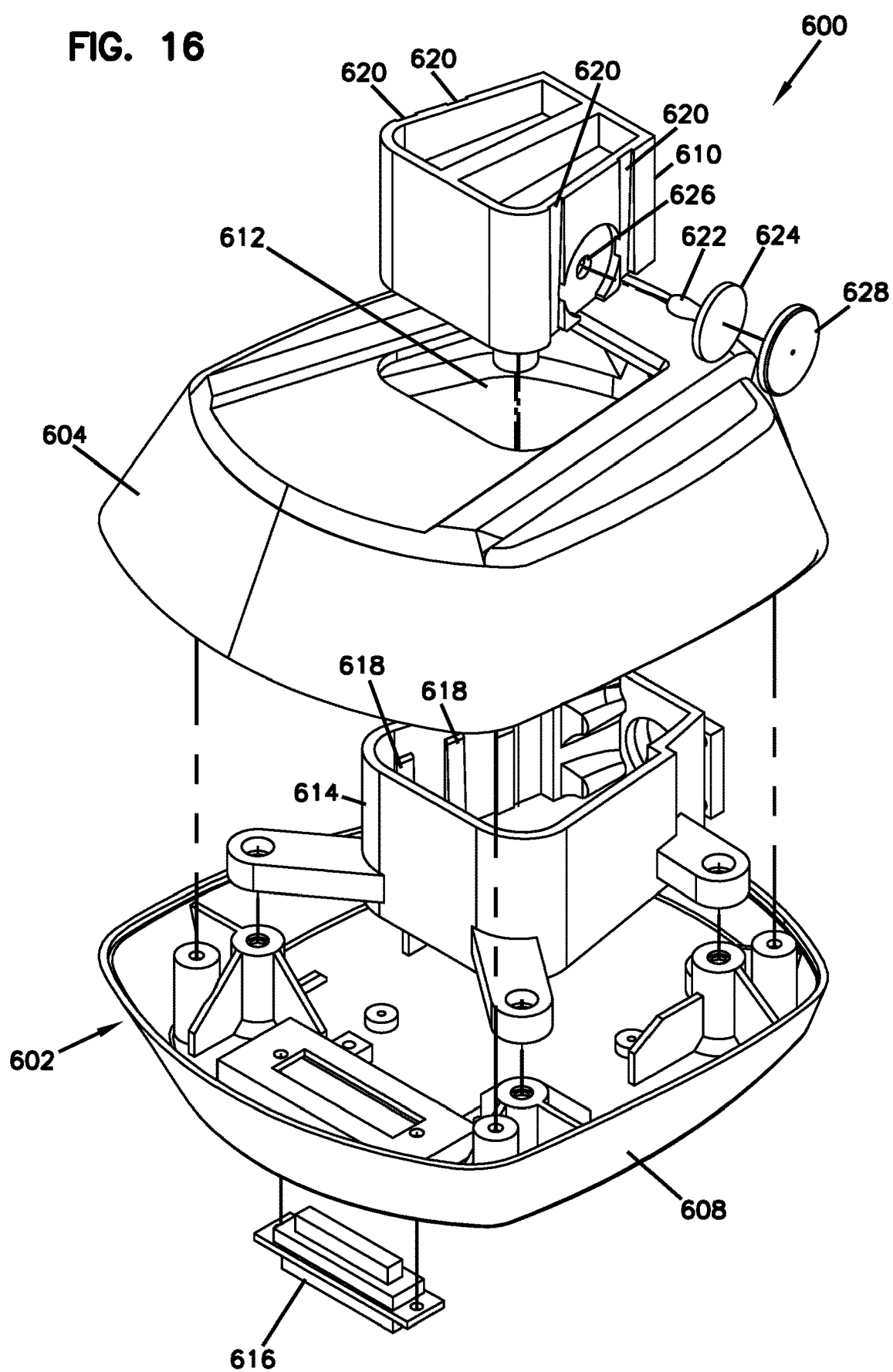

FIG. 20

| Targeting | |
|---|---|
| Instructions | Welcome Andrea<br><br>Required:<br>• Endoscopic camera, light source, and monitor<br>• Hysteroscope (12, 15, 25 or 30 degrees)<br>• Sheath with 5 or 7-Fr channel<br>• Foot pedal (optional)<br><br>Instructions for Targeting:<br>1. Press the START/STOP button or the foot pedal to start exercise.<br>2. Insert the targeting probe into the training box when the countdown commences.<br>3. Identify the first numbered target<br>4. Push the first numbered target with the targeting probe.<br>5. Identify and push the next numbered target.<br>6. Press the START/STOP button or the foot pedal to end exercise. |
| To start: press pedal or button | |
| Complete exercise | |
| Results | |

702 — (table)
704 — Welcome Andrea

FIG. 23

Home > Polyp Transection and Removal    Welcome Andrea 

Polyps
Instructions

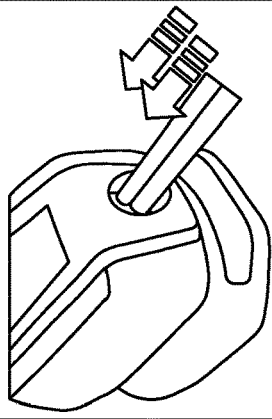

△ To start: press pedal or button
△ Complete exercise
△ Results

Required:
- Endoscopic camera, light source, and monitor
- Hysteroscope (12, 15, 25 or 30 degrees)
- Sheath with 5 or 7-Fr channel
- Foot pedal (optional)
- Pedunculated Polyp or

- Sessile Polyp
- Appropriate polyp canister (right/left; sessile/pedunculated; high or low in the cavity)
- Hysteroscope Scissors (5 or 7 Fr)
- Hysteroscope Grasping Forceps (5 or 7 Fr)
- Appropriate volume measurement template

Instructions for Polyp Transection and Removal:
1. Place the polyp in the appropriate canister and position and secure in the Exercise Module
2. Prepare the hysteroscope, sheath and scissors
3. Press the START/STOP button or the Foot Pedal to start exercise.
4. Insert the hysteroscope/sheath assembly when the countdown completes
5. Identify the polyp
6. Pass the scissors through the operating channel
7. Transect the polyp at base
8. Remove the polyp from the cavity with the grasping forceps
9. Press the START/STOP button or the Foot Pedal to end exercise

FIG. 25

HYSTEROSCOPY TRAINING AND EVALUATION

CROSS-REFERENCE TO RELATED APPLICATIONS

This application claims priority to U.S. Provisional Patent Application 62/575,289 filed Oct. 20, 2017, the disclosure of which is incorporated herein by reference in its entirety.

BACKGROUND

Hysteroscopy is a medical procedure that examines the uterus of a female patient. An instrument called a hysteroscope having an elongated tubular body is inserted through the cervix of the patient for reaching the inside of the uterus. The hysteroscope includes a light and camera at one end for illuminating the uterus and recording images of the uterus that can be transmitted to a monitor. Abnormalities in the uterus can be corrected by inserting small instruments, such as scissors and graspers, through an instrument channel in the hysteroscope. For example, the hysteroscope can be used to remove non-cancerous growths, called polyps, found in the uterus.

In order to minimize life-threatening errors, there is a need for training instruments and testing protocols that simulate hysteroscopic surgery. Such instruments and protocols may ensure that surgeons are proficient at hysteroscopic surgery prior to working on patients. Further, there is a specific need for such instruments and testing protocols in gynecological medicine.

SUMMARY

The present disclosure relates generally to a training device. More specifically, the present disclosure relates to a training device that simulates a gynecological surgery environment that can be used to train and evaluate hysteroscopy medical procedures.

In one aspect, the disclosed technology relates to a system for simulating a medical procedure, the system comprising a base station connected to a computer and monitor, and a training box connected to the base station. The training box includes a housing having a chamber positioned therein, the chamber being adapted to simulate the shape of a uterine cavity and includes an opening for receiving an instrument configured to perform medical training and evaluation exercises inside the chamber.

In another aspect, the disclosed technology relates to a method for simulating a hysteroscopy procedure, the method comprising: providing a base station adapted to communicate with a computer having a monitor, and a training box connected to the base station, the training box includes a housing having a chamber adapted to simulate the shape of a uterine cavity and having one or more numbered targets inside; prompting a test taker to touch a first numbered target inside the chamber using an instrument; detecting whether the test taker has touched the first numbered target; prompting the test taker to touch additional numbered targets using the instrument according to a predefined sequence of number targets; detecting whether the test taker has touched the additional numbered targets according to the predefined sequence of number targets; and displaying the results on the monitor.

In another aspect, the disclosed technology relates to a method for simulating a hysteroscopy procedure, the method comprising: providing a base station adapted to communicate with a computer having a monitor, a training box connected to the base station, the training box including a housing having a chamber adapted to simulate the shape of a uterine cavity and having one or more synthetic polyps; and prompting a test taker to use an instrument to remove the one or more synthetic polyps from the chamber.

A variety of additional aspects will be set forth in the description that follows. The aspects can relate to individual features and to combination of features. It is to be understood that both the foregoing general description and the following detailed description are exemplary and explanatory only and are not restrictive of the broad inventive concepts upon which the embodiments disclosed herein are based.

BRIEF DESCRIPTION OF THE DRAWINGS

FIG. 2A is a view of a hysteroscope used in the exemplary system of FIG. 1.

FIG. 2B is an enlarged view of a portion of the hysteroscope of FIG. 2.

FIG. 3A is a view of a targeting probe that can be used with the hysteroscope of FIG. 2.

FIG. 4D is a view of the forceps equipped with a grasper.

FIG. 4E is a view of the forceps equipped with a serrated cutter.

FIG. 15 is an exploded front perspective view of a training box for a polyp removal exercise.

FIG. 16 is an exploded rear perspective view of the training box of FIG. 15.

FIG. 20 is a view of a software page displayed during a targeting exercise.

FIG. 23 is a view of a software page displayed during a polyp removal exercise.

FIG. 25 is a view of a software page displayed during a polyp removal exercise.

DETAILED DESCRIPTION

Figure 1:
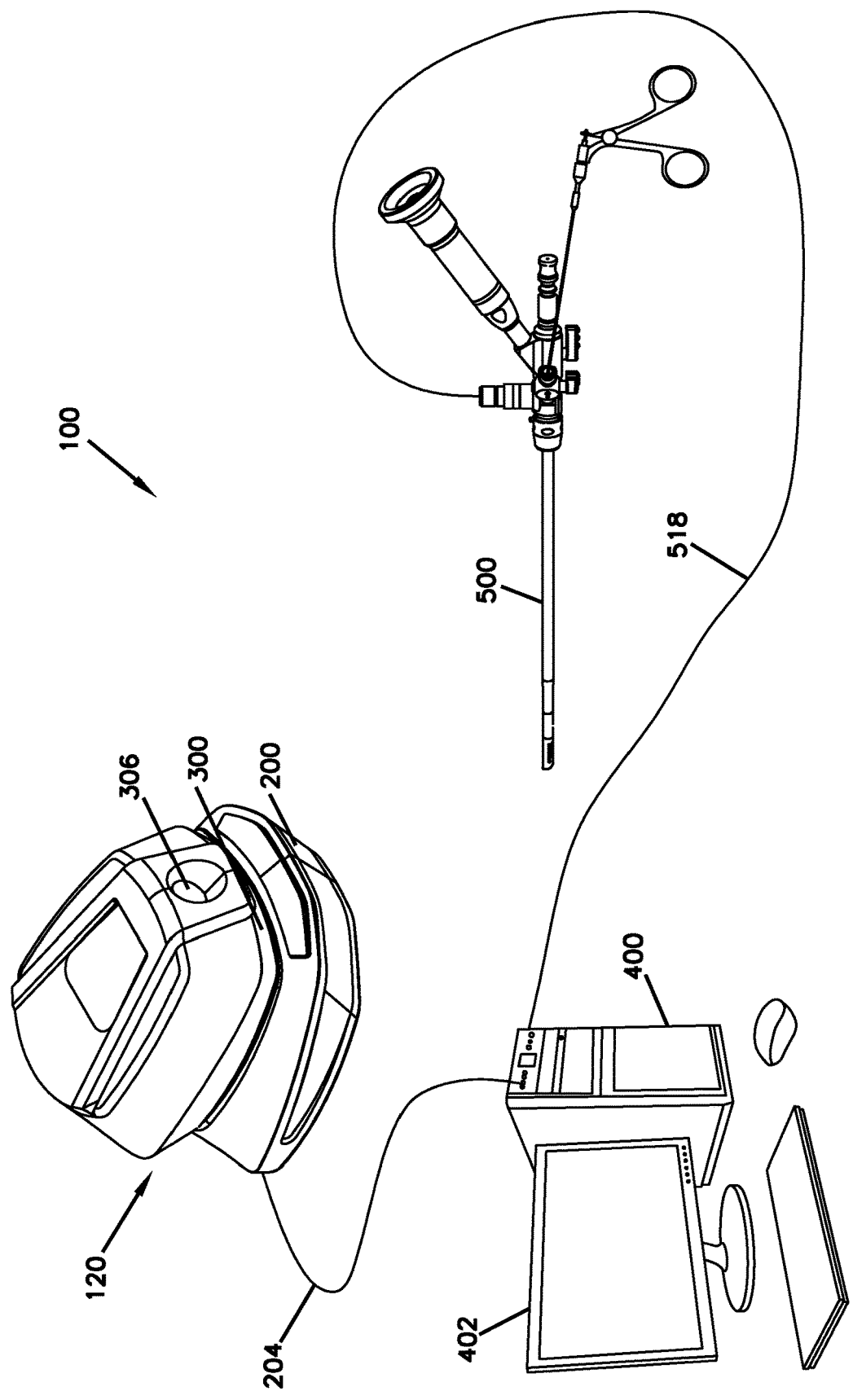
FIG. 1 is a view of an exemplary system for hysteroscopy training and evaluation.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Referring now to FIG. 1, a hysteroscopy training and evaluation system 100 can be used for training and evaluating medical students and medical practitioners including nurses and doctors. In one aspect, the system 100 may be used as part of an exam that evaluates the knowledge and skills of a test taker regarding Obstetrics and Gynecology. The exam may include a cognitive portion having multiple choice questions and a skills portion during which the system 100 may be utilized. In one aspect, the system 100 can be used for certification of obstetricians and gynecologists by the American Board of Obstetrics and Gynecology.

The system 100 includes a simulator 120 having a base station 200 that is electrically and mechanically connected to a training box 300. Evaluation exercises such as targeting and polyp removal exercises can be performed using the simulator 120 for testing instrument handling. In some examples, a single training box can be used to perform multiple evaluation exercises. In other examples, interchangeable training boxes can be attached to the base station 200, each interchangeable training box being dedicated to a unique evaluation exercise.

The base station 200 is connected to a computer 400 having a monitor 402. In some examples, the base station 200 is connected to the computer 400 by a USB cable 204. In other examples, the base station 200 may be connected to the computer 400 via a wireless connection such as Bluetooth. The computer 400 has a processor and a memory, and is adapted to run software interfacing with the base station 200 during various evaluation exercises.

The system 100 also includes a hysteroscope 500 adapted to be inserted into an opening 306 on the front of the training box 300. The hysteroscope 500 is connected to the computer 400 so that video images taken from the hysteroscope 500 inside the training box 300 can be shown on the monitor 402 during evaluation exercises. In some examples, the hysteroscope 500 is connected to the computer 400 by a fiber optic cable 518. In other examples, the hysteroscope 500 may be connected to the computer 400 via a wireless connection such as Bluetooth.

Referring now to FIGS. 2A and 2B, the hysteroscope 500 has an instrument opening 508 adapted to receive various types of instruments that can be used for various evaluation exercises using the simulator 120. An elongated body 502 terminating at a distal end 504 includes an instrument channel 506 that is adapted to receive the various types of instruments inserted through the instrument opening 508. A light 512 and camera 514 are located at the distal end 504 of the body 502. The light 512 is adapted to illuminate an interior of the training box 300 during evaluation exercises, and the camera 514 is adapted to capture and transmit video images to the monitor 402 during the various evaluation exercises performed using the simulator 120.

Figure 3B:
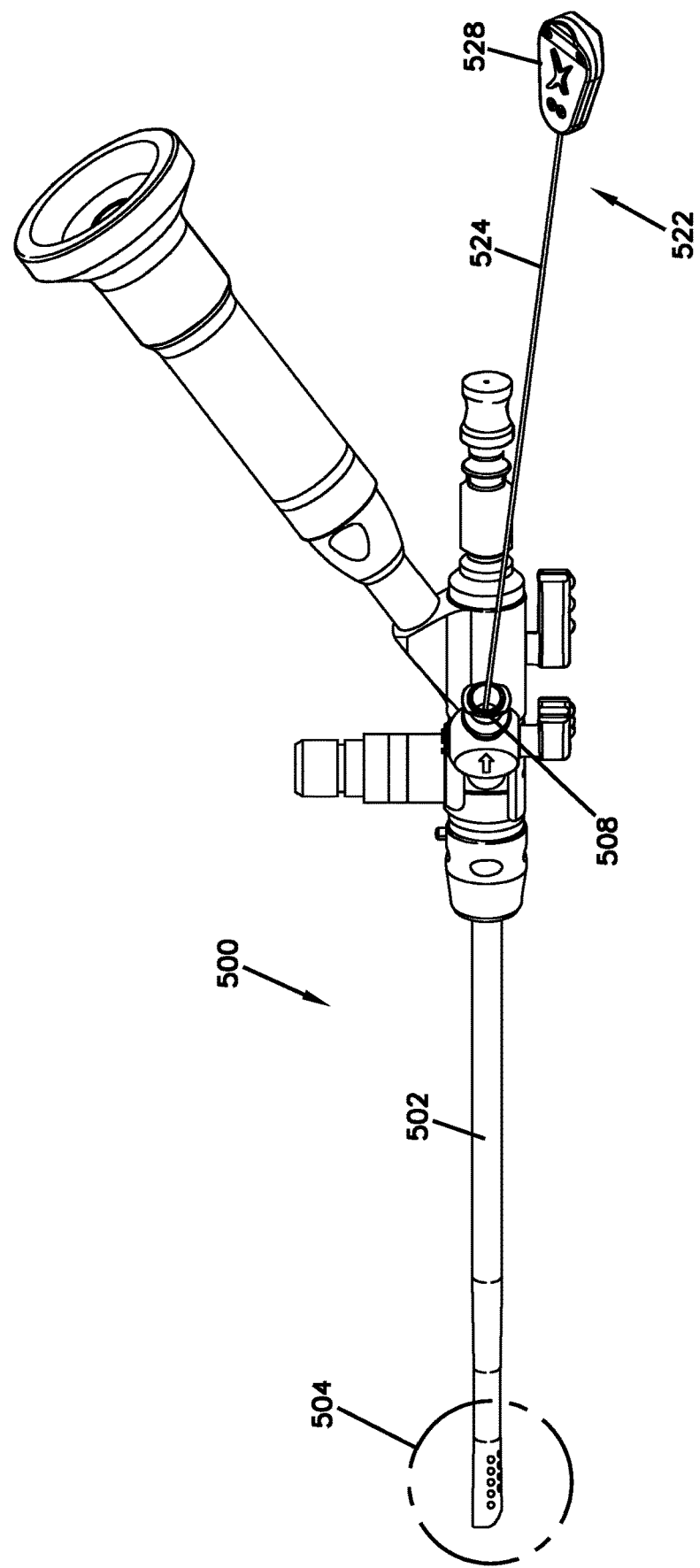
FIG. 3B is a view of the targeting probe inserted in the hysteroscope of FIG. 2.
Figure 3C:
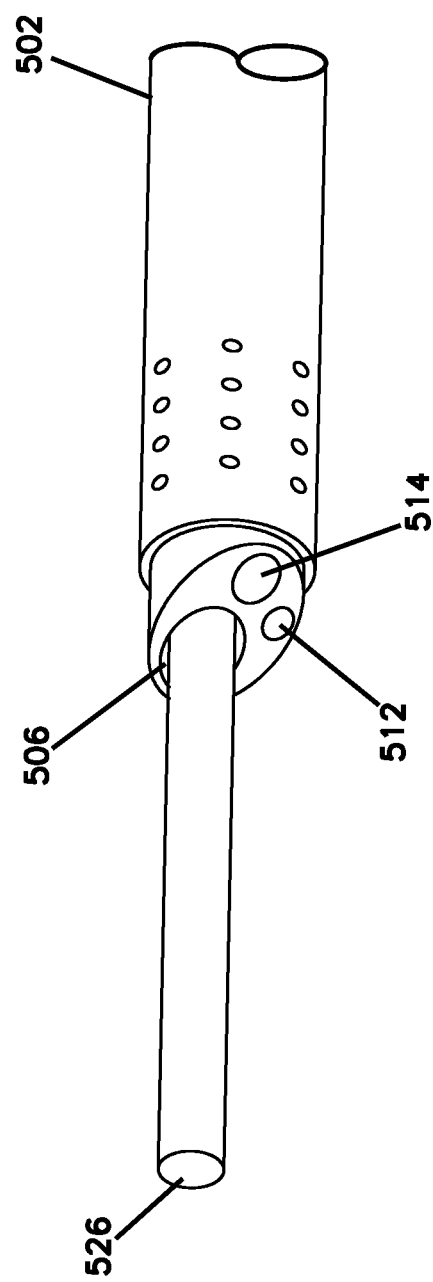
FIG. 3C is an enlarged view of a portion of the hysteroscope of FIG. 2 with the targeting probe inserted therein.

Referring now to FIGS. 3A-3C, the hysteroscope 500 is compatible with a targeting probe 522 for use during a targeting exercise. The targeting probe 522 includes an elongated extension 524 that can be inserted through the instrument opening 508 on the hysteroscope 500. The elongated extension 524 is adapted to extend through the instrument channel 506 for reaching a point beyond the distal end 504 of the hysteroscope 500. The targeting probe 522 includes a handle 528 that can be manipulated by a test taker when holding the hysteroscope 500 for pushing a tip 526 of the targeting probe 522 into an electro-mechanical switch during a targeting exercise. FIG. 3C illustrates the tip 526 of the targeting probe 522 extending through the instrument channel 506 of the hysteroscope 500. In some examples it is contemplated that the targeting probe 522 maybe used without the hysteroscope 500 during a targeting exercise.

Figure 4A:
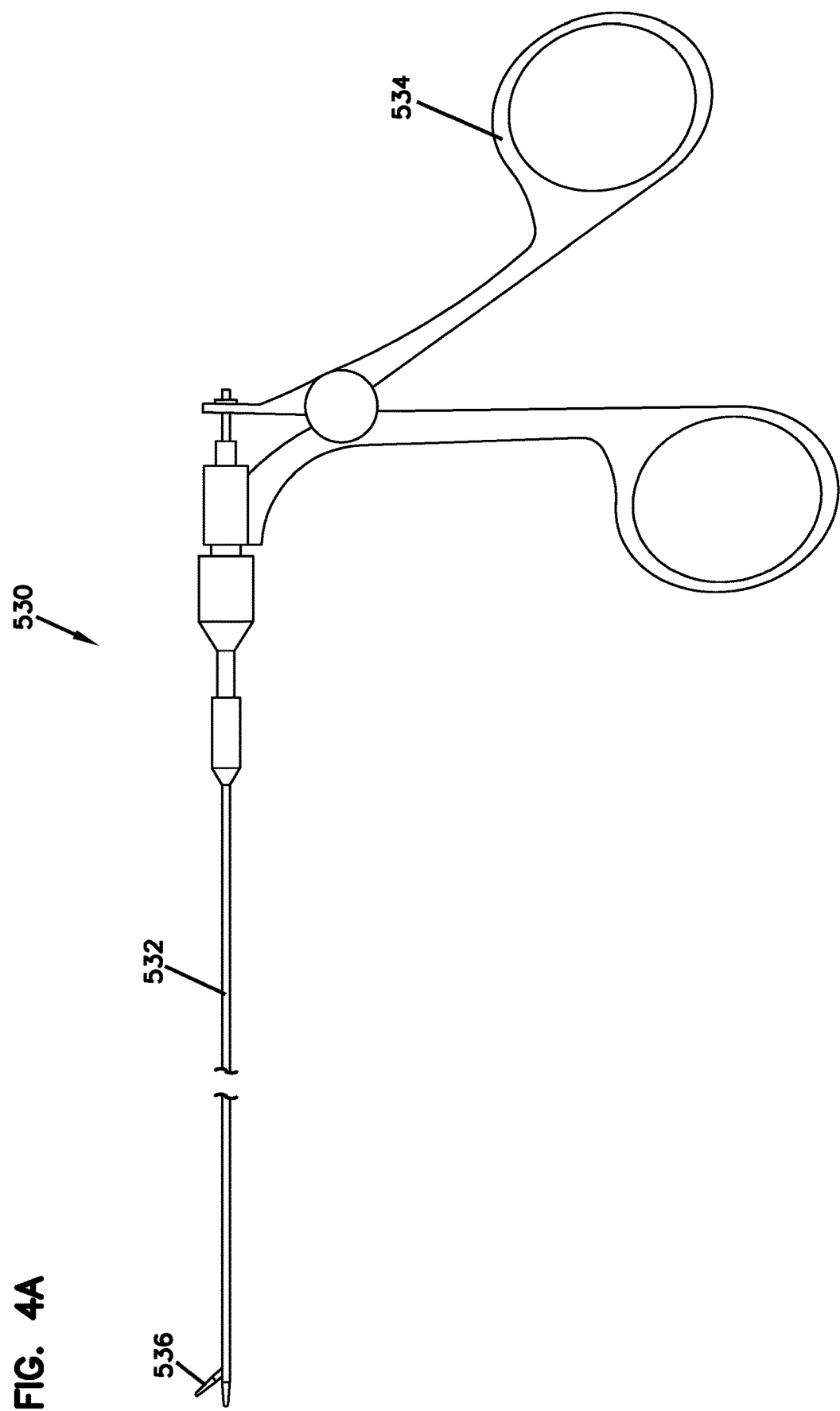
FIG. 4A is a view of a forceps that can be used with the hysteroscope of FIG. 2.
Figure 4B:
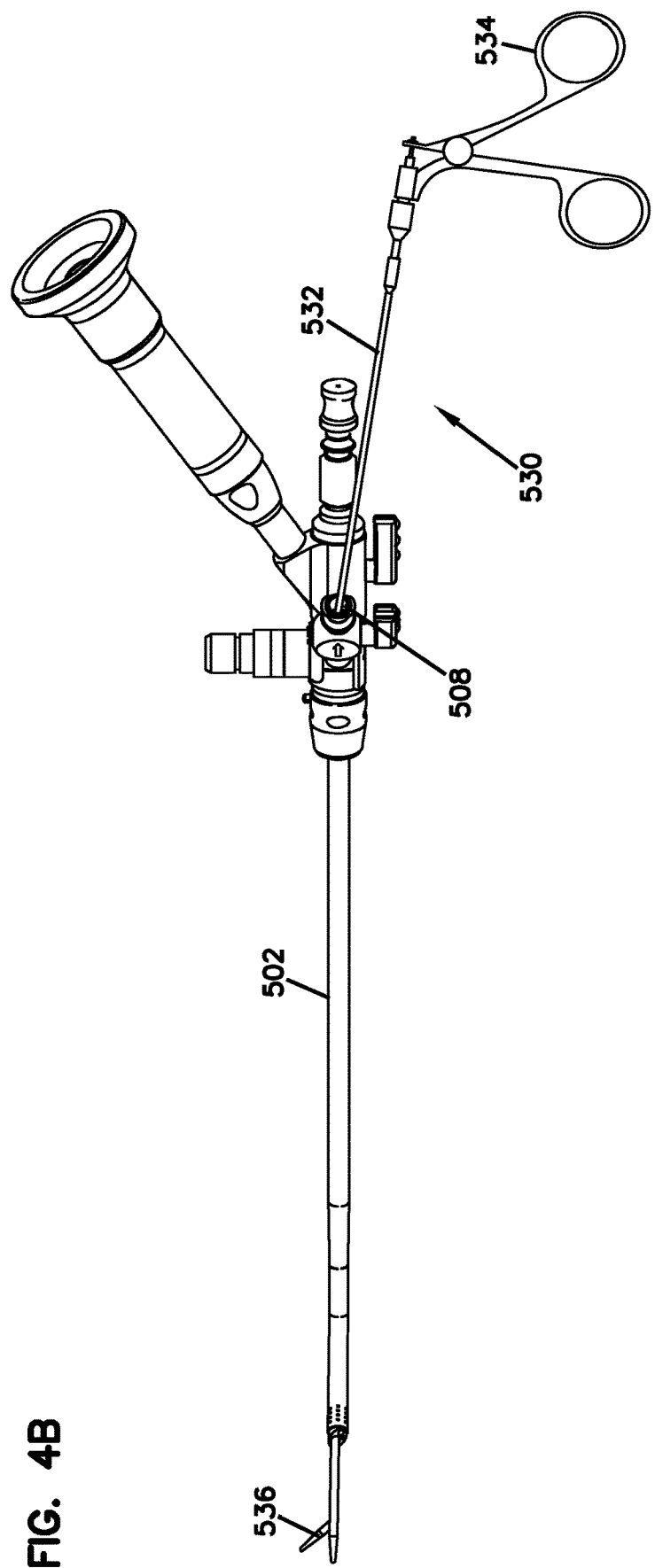
FIG. 4B is a view of the forceps inserted in the hysteroscope of FIG. 2.
Figure 4C:
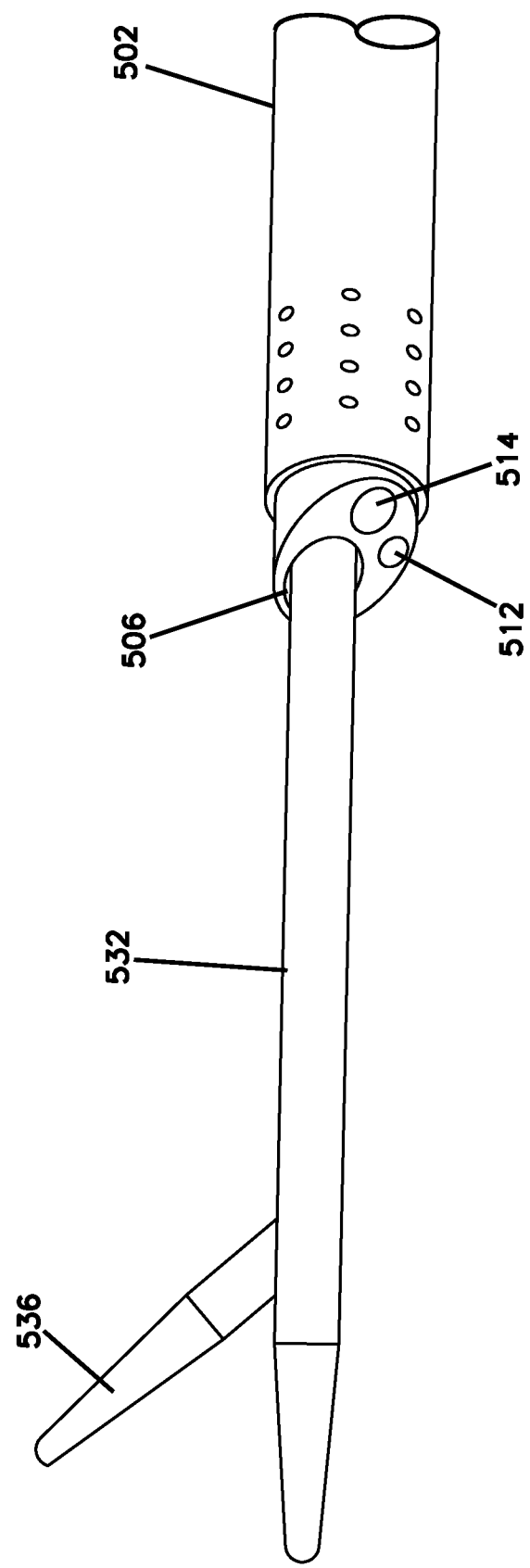
FIG. 4C is an enlarged view of a portion of the hysteroscope of FIG. 2 with the forceps equipped with a scissors inserted therein.

Referring now to FIGS. 4A-4E, the hysteroscope 500 is also compatible with a forceps 530 for use during a polyp removal exercise. Like the targeting probe 522, the forceps 530 includes an elongated extension 532 that can be inserted through the instrument opening 508 for extending through the instrument channel 506 of the hysteroscope 500 and reaching a point beyond the distal end 504 of the hysteroscope 500. The forceps 530 include a handle 534 that can be manipulated by a test taker when holding the hysteroscope 500, and can be equipped with different types of tools at the end of the elongated extension 532. For example, FIGS. 4A-4C depict the forceps 530 equipped with a scissors 536. Alternatively, the forceps can be equipped with a grasper 538 (FIG. 4D) or a serrated cutter 540 (FIG. 4E) instead of the scissors 536.

Figure 5:
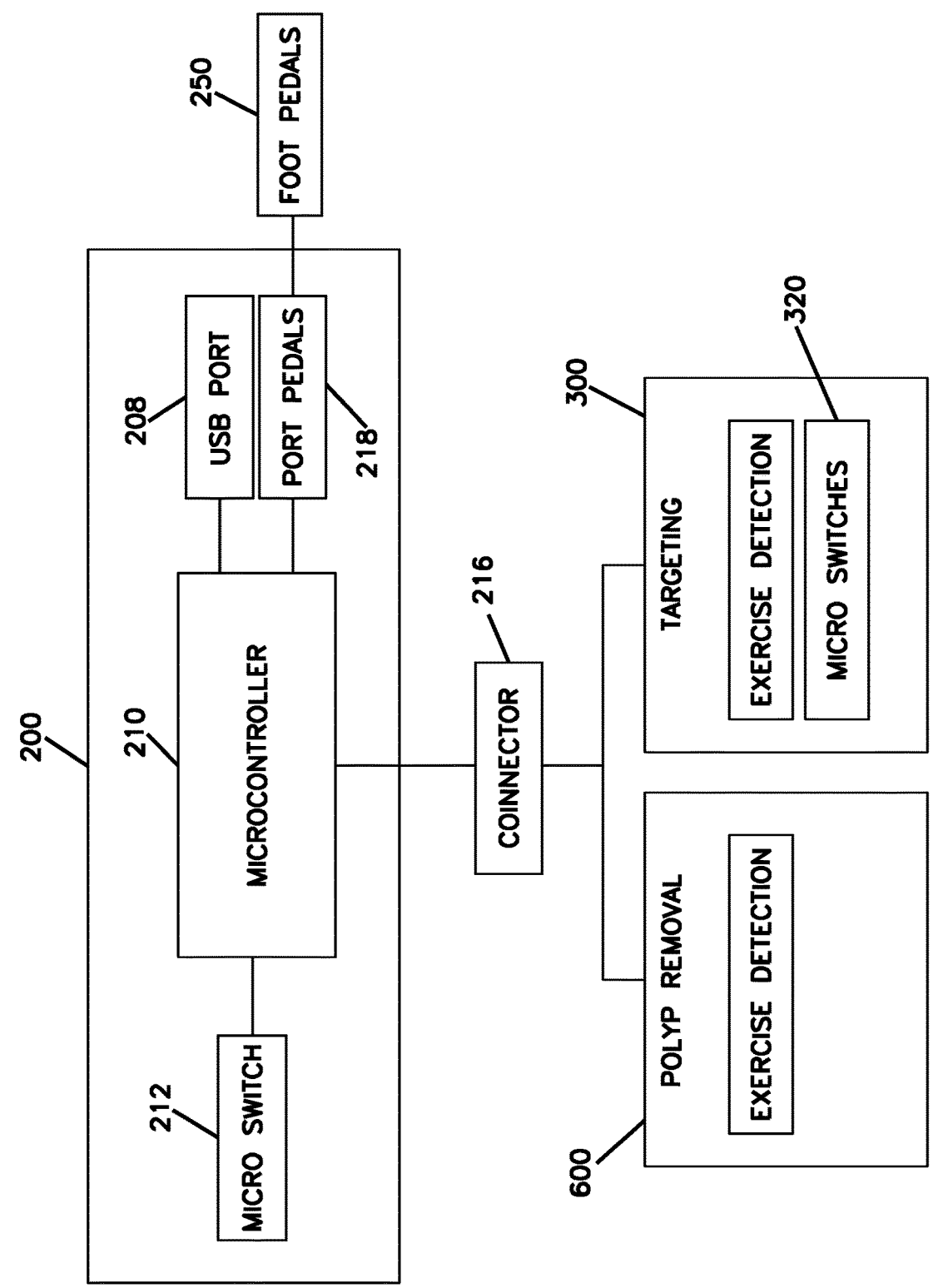
FIG. 5 is a block diagram of electrical components for a simulator used in the exemplary system of FIG. 1.

Referring now to FIG. 5, the base station 200 includes a microcontroller 210 adapted to run software for executing evaluation exercises, storing data (e.g., the results) from the evaluation exercises, and processing data from the evaluation exercises. The microcontroller 210 of the base station 200 may be activated by pressing a start button 212 or stepping on a foot pedal 250 which are described in more detail below. The microcontroller 210 may be connected via an electrical connector 216 to a training box 300 for targeting exercises or to a training box 600 for polyp removal evaluation exercises. The microcontroller 210 is adapted to detect whether a training box 300 for the targeting exercise is connected to the base station 200 or whether a training box 600 for polyp removal evaluation exercises is connected to the base station 200. In some examples, the microcontroller 210 determines which training box 300, 600 is connected to the base station 200 by sensing a unique combination of high-voltage pins.

Figure 6:
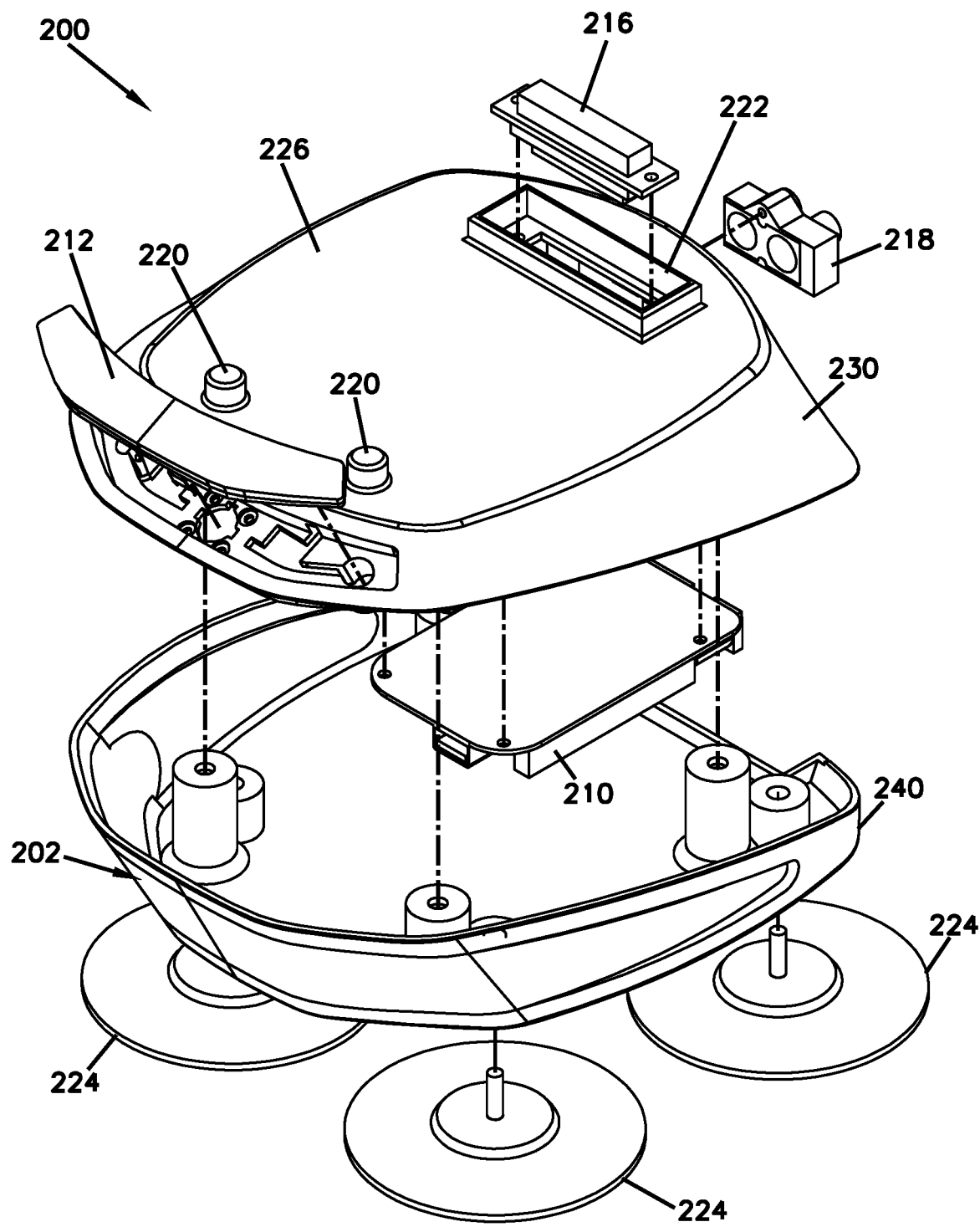
FIG. 6 is an exploded front perspective view of a base station for a simulator used in the exemplary system of FIG. 1.
Figure 7:
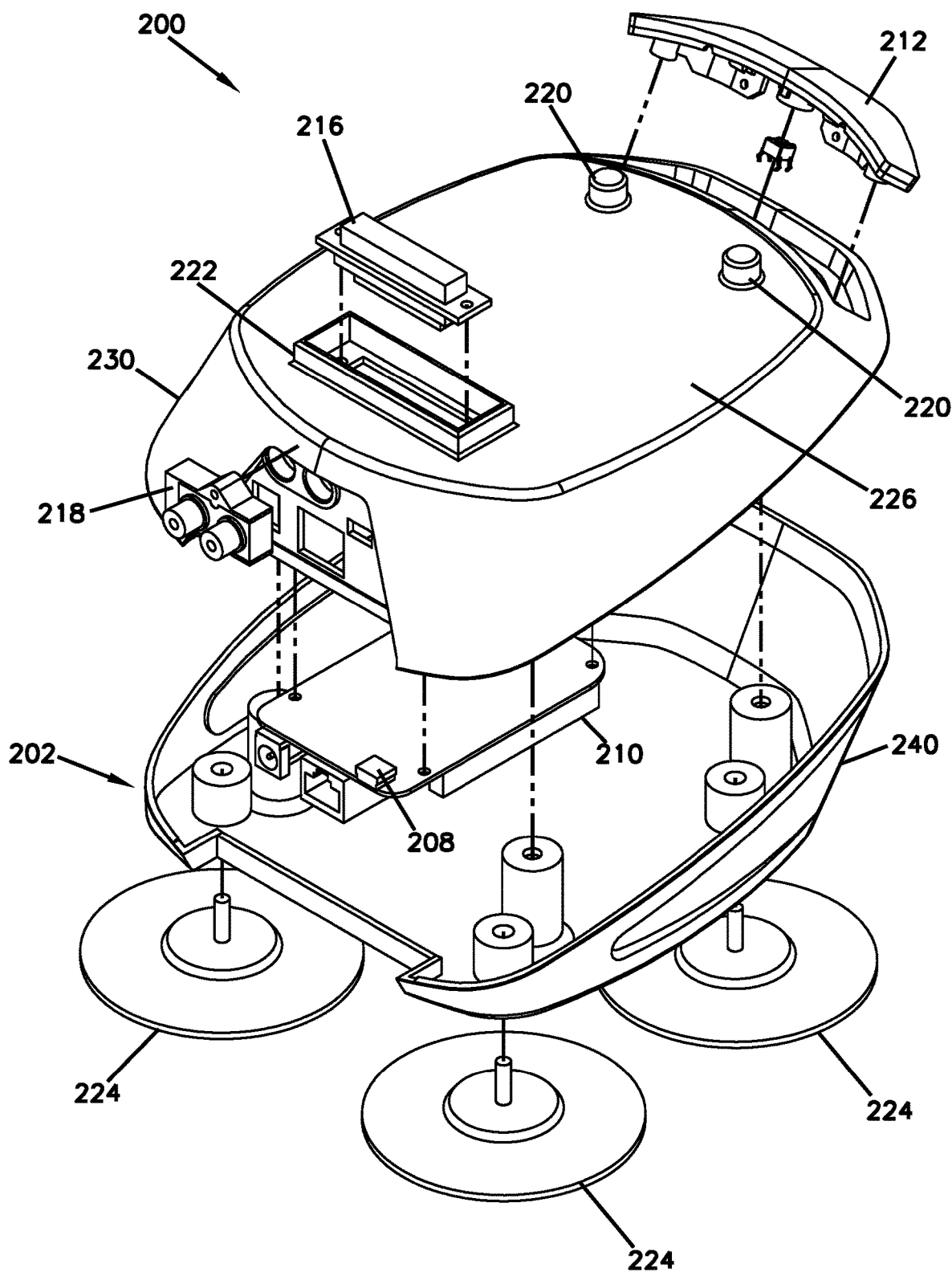
FIG. 7 is an exploded rear perspective view of the base station of FIG. 6.
Figure 8:
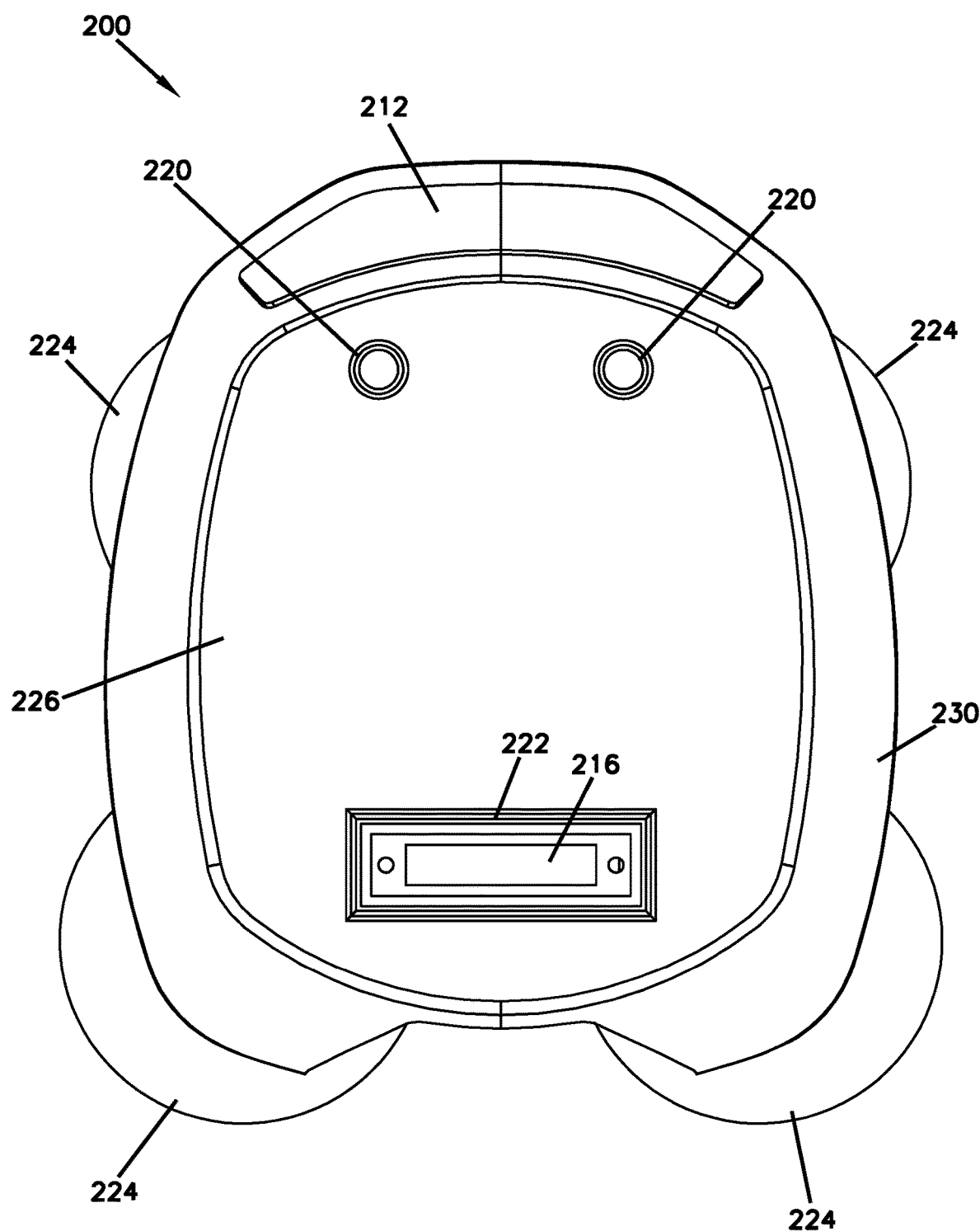
FIG. 8 is a top view of the base station of FIG. 6.

Referring now to FIGS. 6-8, the base station 200 includes a housing 202 having a top shell 230 and a bottom shell 240. A USB port 208 (depicted in FIG. 7) is adapted to receive the USB cable 204 (depicted in FIG. 1) for connecting the microcontroller 210 of the base station 200 to the computer 400. When connected to the computer 400 via the USB cable 204, the computer 400 acts as both a power supply and user interface for the simulator 120.

In some examples, the electrical connector 216 of the base station 200 is adapted to mate with a corresponding electrical connector on the training box for creating an electrical connection between the base station 200 and the training box. The electrical connection enables the microcontroller 210 of the base station 200 to communicate with the training box so that the base station 200 can receive sensor signals from the training box. In some examples, the electrical connector 216 is a female 25-pin D-Sub connector.

In addition to the electrical connector 216, the base station 200 also includes mechanical connectors for mechanically connecting the training box 300 to the base station 200 so that the training box 300 does not move relative to the base station 200 during an evaluation exercise. The mechanical connectors may include pegs 220 and an edge 222 around the electrical connector 216 on a top surface 226 of the base station 200. The pegs 220 and edge 222 are adapted to fit tightly into corresponding cavities on a bottom surface of the training box 300. It is contemplated that the shape and size of the pegs 220 and edge 222, as depicted in the figures, may vary as needed or desired for a particular application.

Figure 9A:
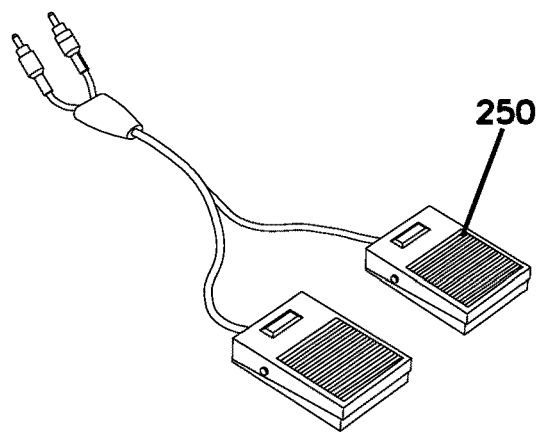
FIG. 9A is a view of an optional foot pedal for the base station of FIG. 6.
Figure 9B:
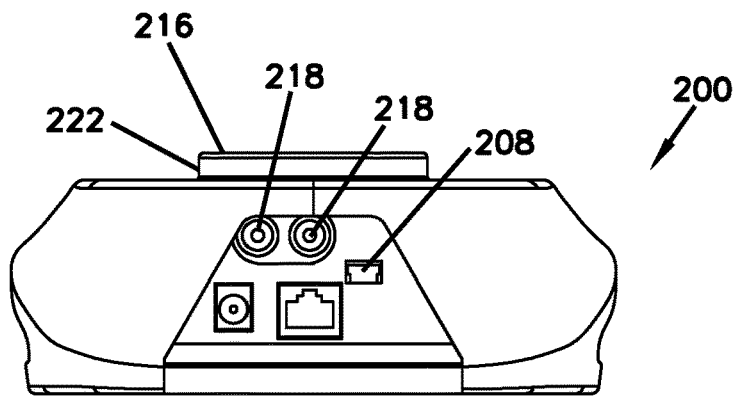
FIG. 9B is a rear view of the assembled base station of FIG. 6.
Figure 9C:
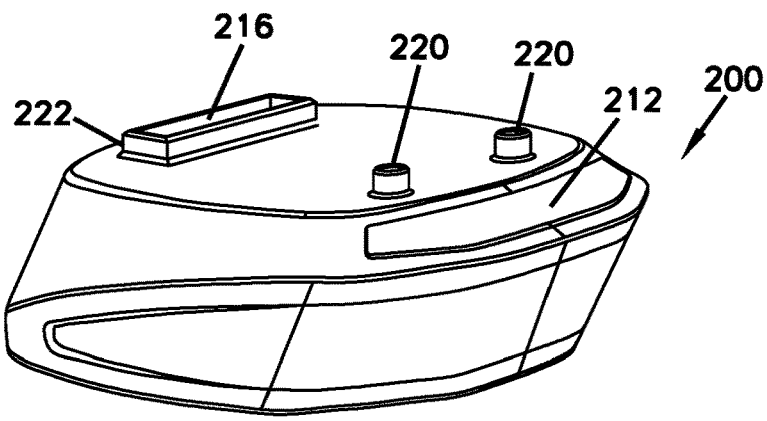
FIG. 9C is an assembled front perspective view of the base station of FIG. 6.

Still referring to FIGS. 6-8, the base station 200 includes a start button 212 that initiates an evaluation exercise when pressed by the test taker. The start button 212 may also be used to end an evaluation exercise. Referring now to FIGS. 9A-9C, the base station 200 may also include pedal cable ports 218 for connecting an optional foot pedal 250 to the base station 200. When pressed by the test taker's foot, the optional foot pedal 250 can be used to either start or end an evaluation exercise instead of, or in addition to, the start button 212.

In some examples, the base station 200 may include supports 224 for anchoring the base station 200 to a flat surface such as an examination table. A test taker will typically sit in front of the examination table so that the test taker can insert an instrument such as the hysteroscope 500 into the opening 306 of the training box 300 during an evaluation exercise. The supports 224 may help prevent the simulator 120 from moving when forces are applied to the simulator 120 by a test taker during an evaluation exercise. In some examples, the supports 224 are plastic or rubber suction cups adapted to secure the base station 200 to the examination table.

Figure 10:
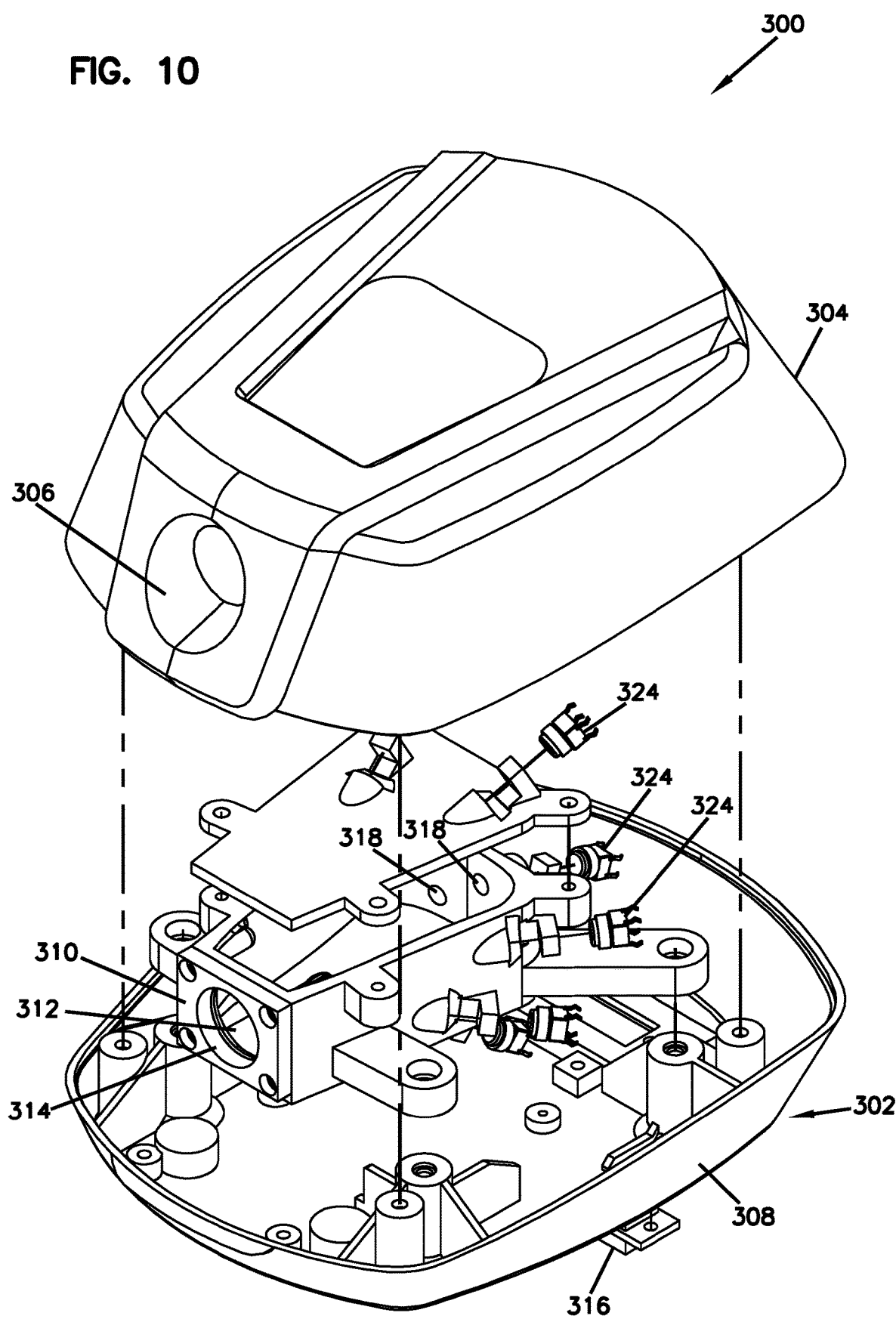
FIG. 10 is an exploded front perspective view of a training box for a targeting exercise.
Figure 11:
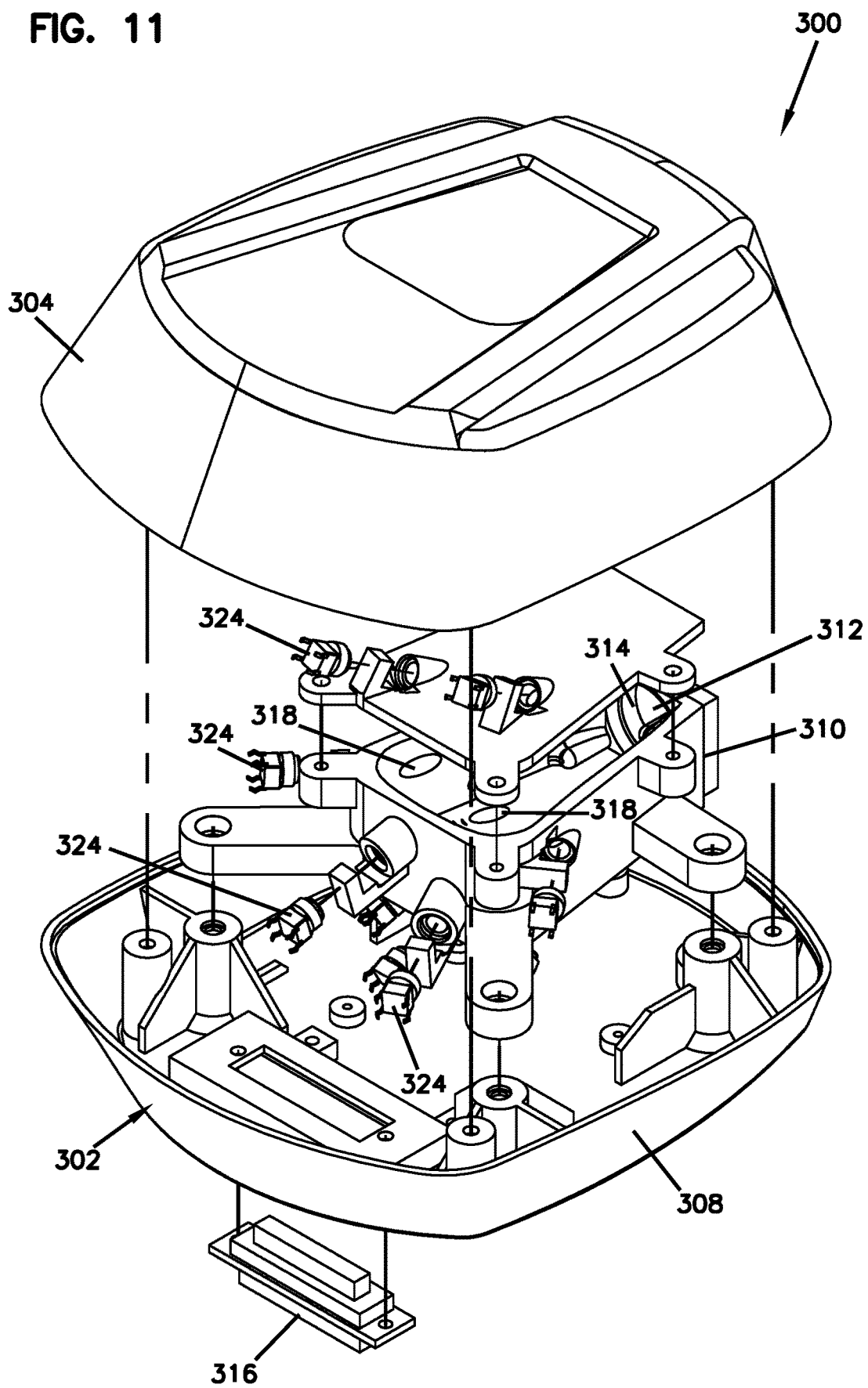
FIG. 11 is an exploded rear perspective view of the training box of FIG. 10.
Figure 12:
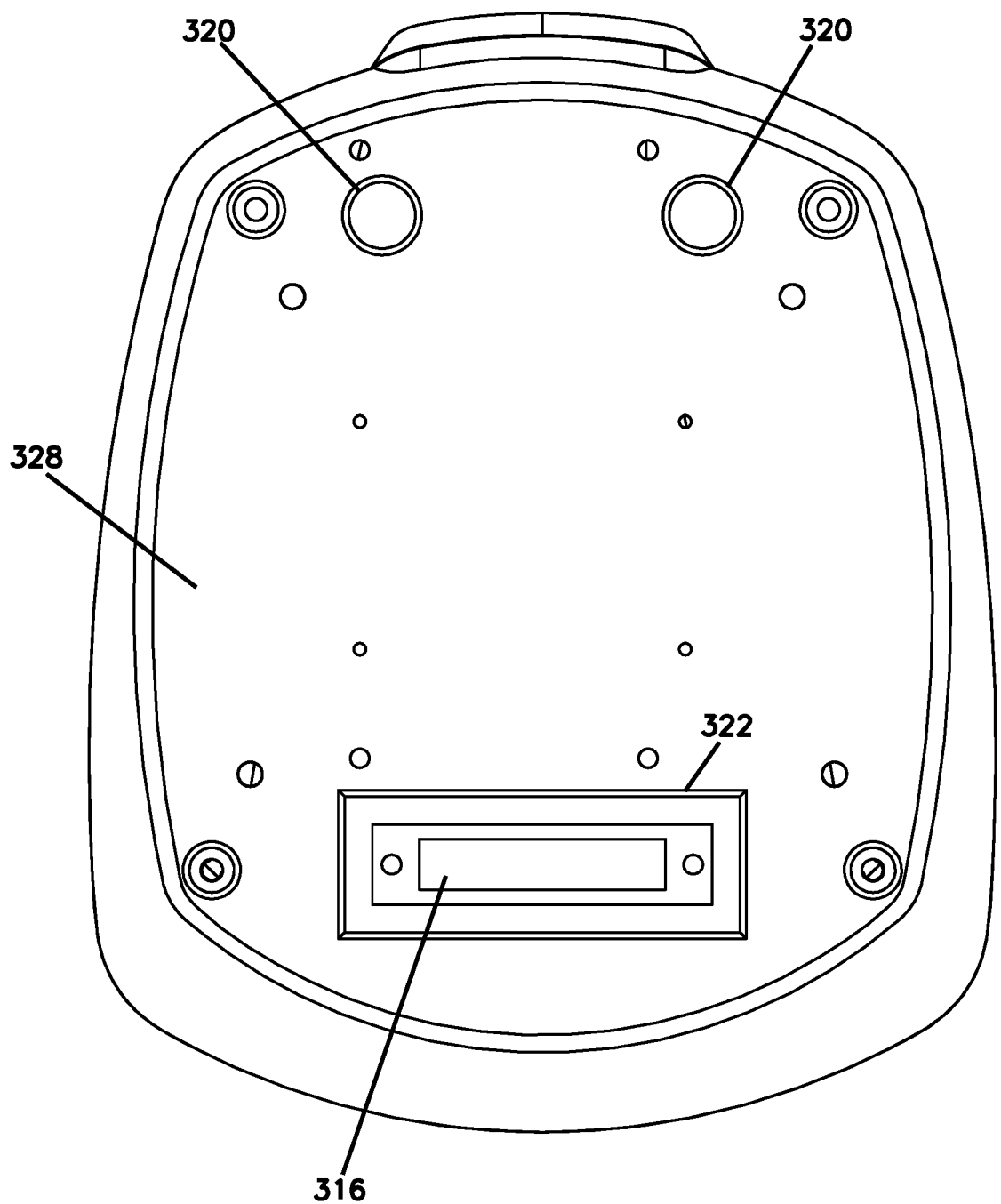
FIG. 12 is a bottom view of the training box of FIG. 10.

Referring now to FIGS. 10-12, a training box 300 for targeting exercises has an electrical connector 316 adapted to connect to the electrical connector 216 of the base station 200 so that data communication is transmitted between the training box 300 and the base station 200. In some examples, the electrical connector 316 is a male 25-pin D-Sub connector.

The training box 300 includes a housing 302 having a top shell 304 and a bottom shell 308. A chamber 310 simulating the shape of a female uterus is fixed to the housing 302. The chamber 310 has an opening 312 that aligns with the opening 306 on the exterior of the training box 300 when the top and bottom shells 304, 308 are attached to one another. The opening 306 of the training box 300 may simulate the shape of a female vagina. A canal 314 extending from the opening 312 of the chamber 310 may simulate the shape of a female cervix. The top and bottom shells 304, 308 can be made from a rigid material, whereas the opening 312 and the canal 314 of the chamber 310 can be made from a flexible material and can allow for angular repositioning of the hysteroscope 500 when inserted inside the training box 300.

Sensors are adapted to detect when the targeting probe 522 has touched a numbered target 318 inside the chamber 310. In some examples, the sensors are electro-mechanical switches 324 that are activated when touched by the tip 526 of the targeting probe 522. The electro-mechanical switches 324 are adapted to transmit a signal to the base station 200 via the electrical connector 316. The base station 200 can then forward this data to the computer 400 for display on the monitor 402. For example, in addition to displaying the video images taken from the hysteroscope 500, the monitor 402 may also include icons representing a plurality of numbered targets 318, and each icon can change color after an associated numbered target 318 is touched by the targeting probe 522.

Referring now to FIG. 12, a bottom surface 328 of the training box 300 includes cavities 320 that correspond to the shape of the pegs 220 on the top surface 228 of the base station 200. The bottom surface 328 also includes a cavity 322 that corresponds to the shape of the edge 222 on the top surface 228 of the base station 200. The bottom surface 328 also includes the electrical connector 316 adapted to connect to the electrical connector 216 of the base station 200.

Figure 13:
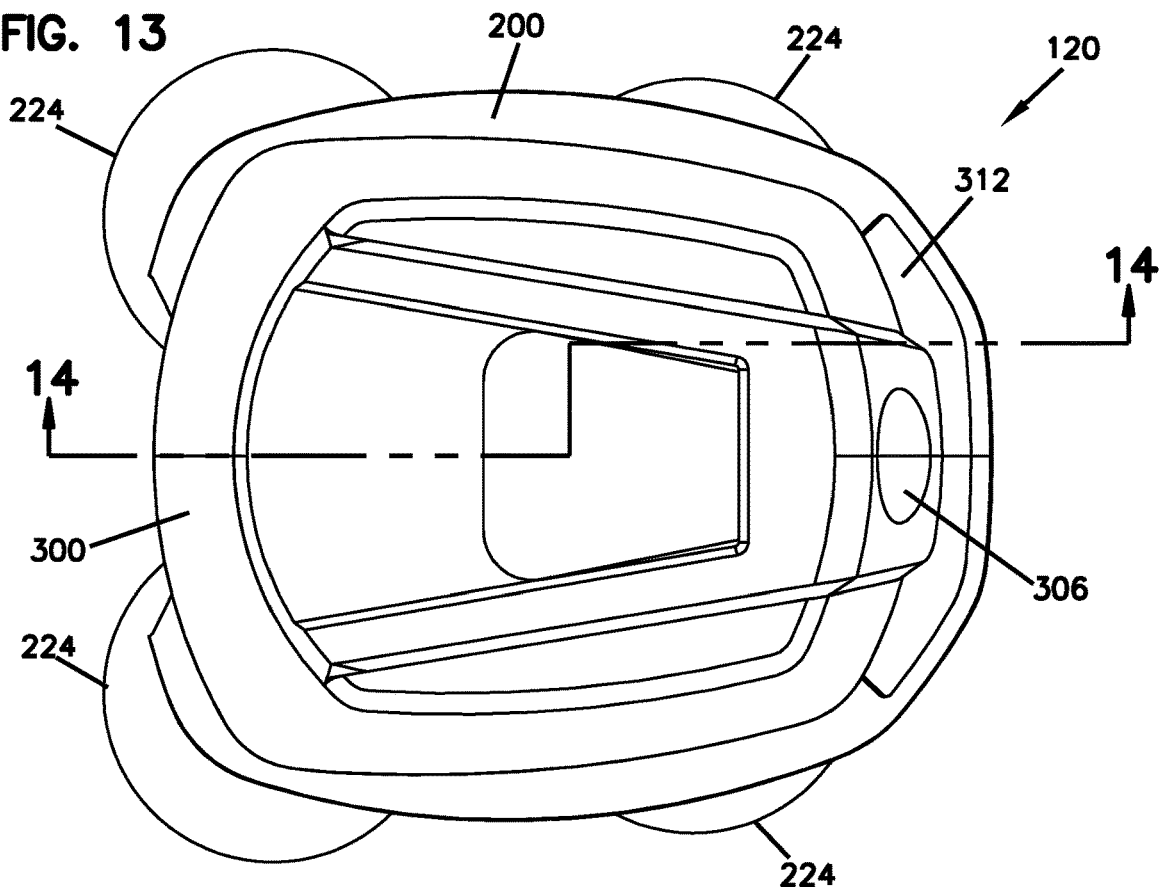
FIG. 13 is a top view of the simulator of FIG. 1 having the training box of FIG. 10 attached to the base station of FIG. 6.
Figure 14:
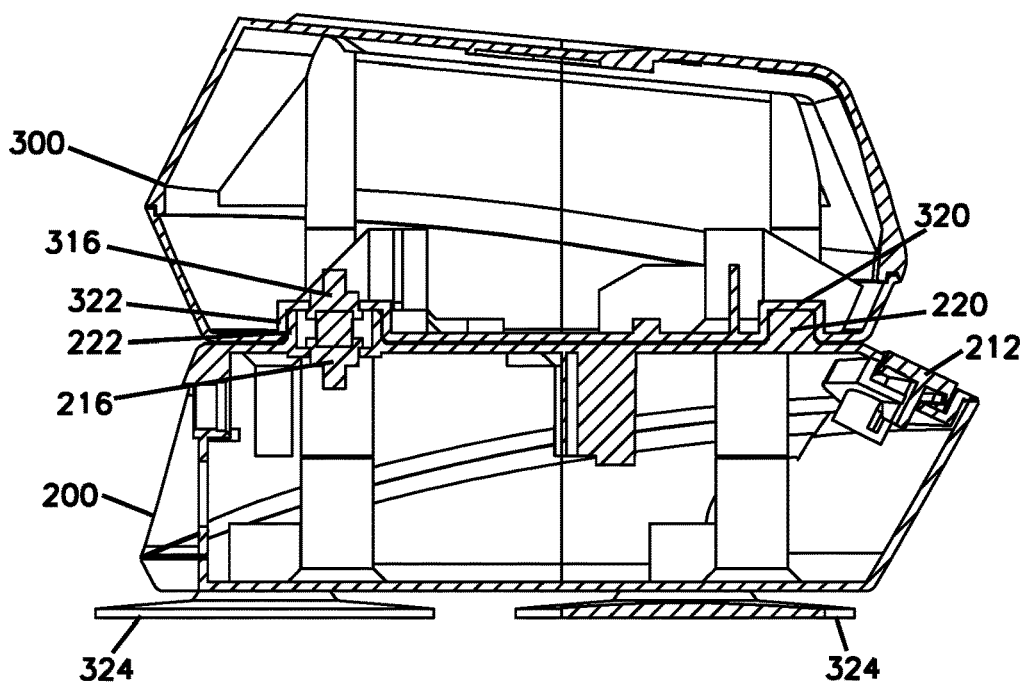
FIG. 14 is a sectional view of the simulator of FIG. 13 along the line A-A.

Referring now to FIGS. 13 and 14, a mechanical coupling is established between the training box 300 and the base station 200 when the pegs 220 and edge 222 of the base station 200 are inserted into the cavities 320, 322 of the training box 300. Accordingly, the bottom surface 328 of the training box 300 is adapted to mechanically connect to the top surface 228 of the base station 200. As described above, the supports 224 anchor the base station 200 to a flat surface such as an examination table. Furthermore, the electrical connector 316 of the training box 300 when connected to the electrical connector 216 of the base station 200 establishes data communication between the training box 300 and the base station 200.

Referring now to FIGS. 15 and 16, a training box 600 for polyp removal evaluation exercises shares many similar components with the training box 300. The training box 600 includes an electrical connector 616 adapted to connect to the electrical connector 216 of the base station 200 for establishing data communication between the training box 600 and the base station 200. In some examples, the electrical connector 616 is a male 25-pin D-Sub connector.

The training box 600 includes a housing 602 having a top shell 604 and a bottom shell 608. An opening 612 is located on the top shell 604 for receiving a chamber 610. The chamber 610 is secured to an internal frame 614 fixed to the housing 602 of the training box 600. The chamber 610 may have a series of slots 620 that correspond with a series of ribs 618 disposed on one or more sides of the internal frame 614 for securing the chamber 610 to the internal frame 614 so that the chamber 610 does not move during a polyp removal exercise while also allowing the chamber 610 to be removed from the training box 600 through the opening 612 after the polyp removal exercise is completed. The chamber 610 has an opening 630 that aligns with the opening 606 located on the front of the training box 600. Optionally, a cover may be placed over the opening 612 for concealing the chamber 610 when held inside the training box 600.

One or more synthetic polyps 622 may be inserted into the chamber 610. For example, a synthetic polyp 622 attached to a plate 624 can be inserted through an opening 626 (depicted in FIG. 16) disposed on a surface of the chamber 610. A cover plate 628 may be fitted to the surface of the chamber 610 for securing the synthetic polyp 622 and the plate 624 to the chamber 610. In some examples, the chamber 610 includes only one synthetic polyp 622. In other examples, the chamber 610 includes multiple synthetic polyps 622. The synthetic polyps 622 may be inserted on the left, right, bottom, top, and rear surfaces of the chamber 610.

Figure 17A:
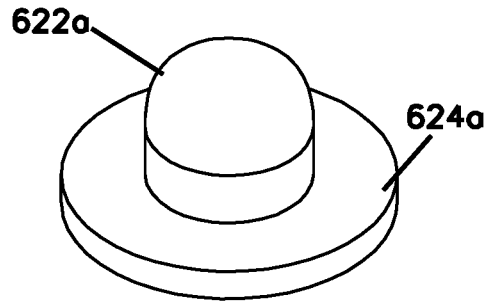
FIG. 17A is perspective view of a fat synthetic polyp.
Figure 17B:
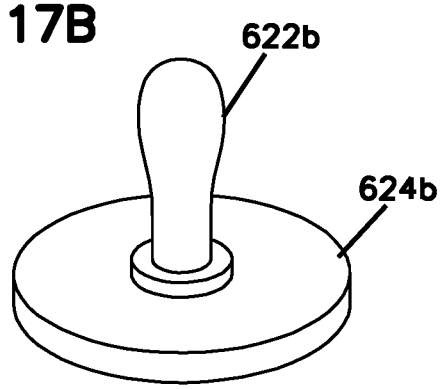
FIG. 17B is a perspective view of a thin synthetic polyp.
Figure 18A:
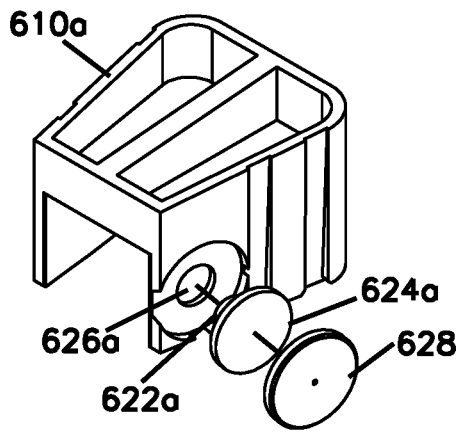
FIG. 18A is an exploded view of a chamber having the fat synthetic polyp of FIG. 16A.
Figure 18B:
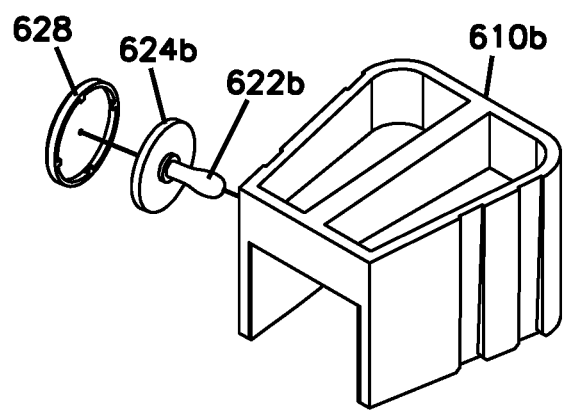
FIG. 18B is an exploded view of a chamber having the thin synthetic polyp of FIG. 16B.

Referring now to FIGS. 17A and 17B, the synthetic polyps may have different shapes and sizes. For example, a fat synthetic polyp 622a having a thick diameter can be attached to a plate 624a, and a thin synthetic polyp 622b having a thin diameter can be attached to a plate 624b. Referring now to FIGS. 18A and 18B, in some examples different types of chambers 610 can be used in combination with the training box 600. For example, a chamber 610a (depicted in FIG. 18A) may have a large opening 626a on a side of the chamber 610a for fitting the fat synthetic polyp 622a. Similarly, a chamber 610b (depicted in FIG. 18B) may have a small opening 626b on a side of the chamber 610b for fitting the thin polyp 622b. In both chambers 610a and 610b, the synthetic polyps 622a, 622b are secured by a cover plate 628 which keeps the polyps 622a, 622b in place while inserting the chamber 610 into the training box 600.

It has been found to be advantageous to make the synthetic polyps 622a, 622b from certain materials so that they have the shape, texture, and feel of an actual polyp. In some examples, the synthetic polyps 622a, 622b may be made from a silicon material.

Figure 19:
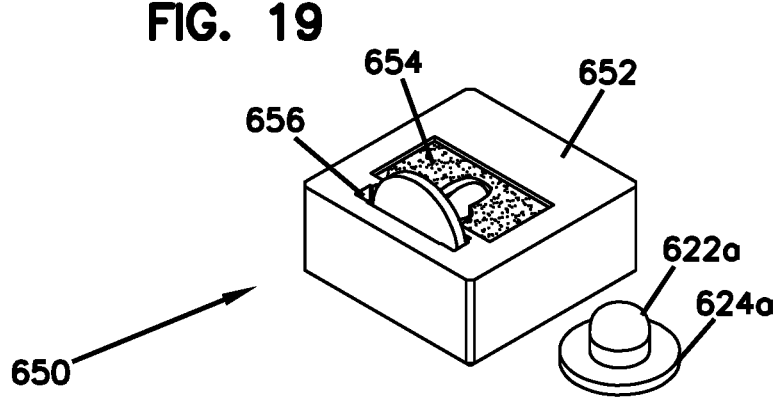
FIG. 19 is a perspective view of a polyp measuring station.

Referring now to FIG. 19, a polyp measuring station 650 may be used to measure a cut made on a synthetic polyp 622a, 622b after completion of the polyp removal evaluation exercise. The polyp measuring station 650 has a body 652 that encapsulates a core 654 and a slot 656 for receiving the plate 624a, 624b attached to the synthetic polyp 622a, 622b. By pushing the plate 624a, 624b into the slot 656 and pressing the synthetic polyp 622a, 622b into the core 654, the cut made on the synthetic polyp 622a, 622b during a polyp removal exercise can be measured.

Targeting Exercise

Referring now to FIG. 20, a targeting exercise can be performed using the simulator 120 fitted with the training box 300 and the targeting probe 522. On the monitor 402, a software page 702 is opened for providing instructions 704 for the targeting exercise. The objective of the targeting exercise is to target and push a sequence of numbered targets 318 inside the chamber 310 of the training box 300 using the targeting probe 522. The numbered targets 318 may be located on different surfaces of the chamber 310. For example, the numbered targets 318 may be located in areas representing the anterior, posterior, lateral, and corneal (i.e., near the fallopian tube entrance) areas of a simulated uterine cavity defined by the chamber 310. The time allotment for completing the exercise and the sequence in which the numbered targets 318 are to be pushed can be set by an administrator or proctor of the targeting exercise.

Figure 21:
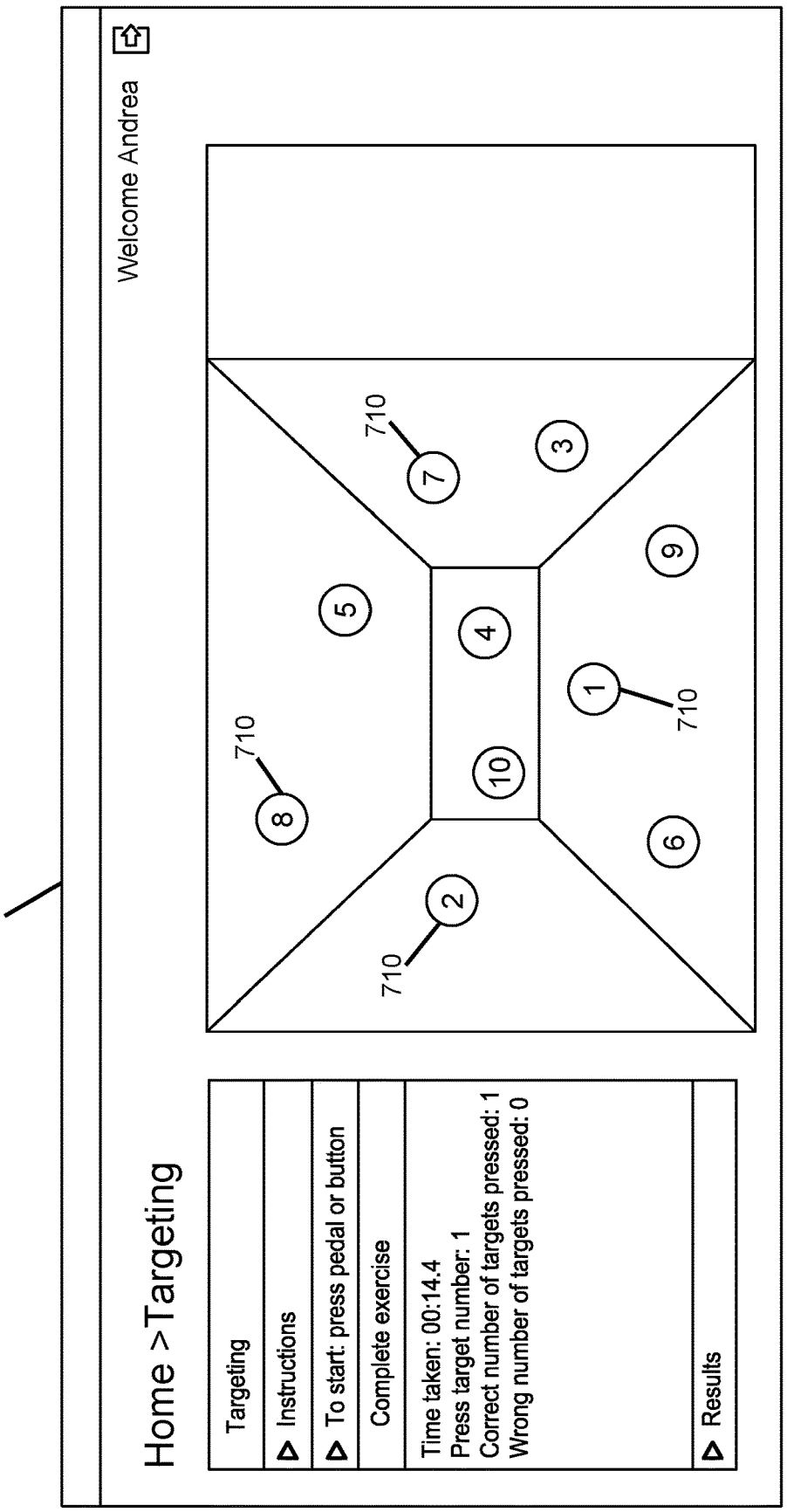
FIG. 21 is view of another software page displayed during a targeting exercise.

Referring now to FIG. 21, the targeting exercise begins and a new software page 708 is opened on the monitor 402 after the test taker presses the start button 212 or steps on the foot pedal 250. The software page 708 includes several icons 710 representing the numbered targets 318 inside the chamber 310, and indicates if a numbered target 318 is successfully touched in the correct sequence by changing the color of the icon 710. For example, each icon 710 representing a numbered target 318 may have an original color or no color at all, and may change to a green color (or some other color) when successfully touched in sequence. Conversely, the icons 710 can change color to indicate that they have been incorrectly touched out of sequence. For example, an icon 710 can change to a red color (or some other color) if incorrectly touched.

During the targeting exercise, the test taker is prompted to touch a first numbered target 318 inside the chamber 310. In some examples, the test taker can use the light 512 and camera 514 of the hysteroscope 500 to illuminate the interior of the chamber 310, and can view the interior of the chamber 310 by looking at the monitor 402 which may include a split screen showing the interior of the chamber 310 in addition to the software page 708. Once the test taker has located and has successfully touched the first numbered target 318 with the targeting probe 522, the test taker must then touch, in the correct sequence, a second numbered target 318, a third targeted number 318, and so on for completing the targeting exercise.

Figure 22:
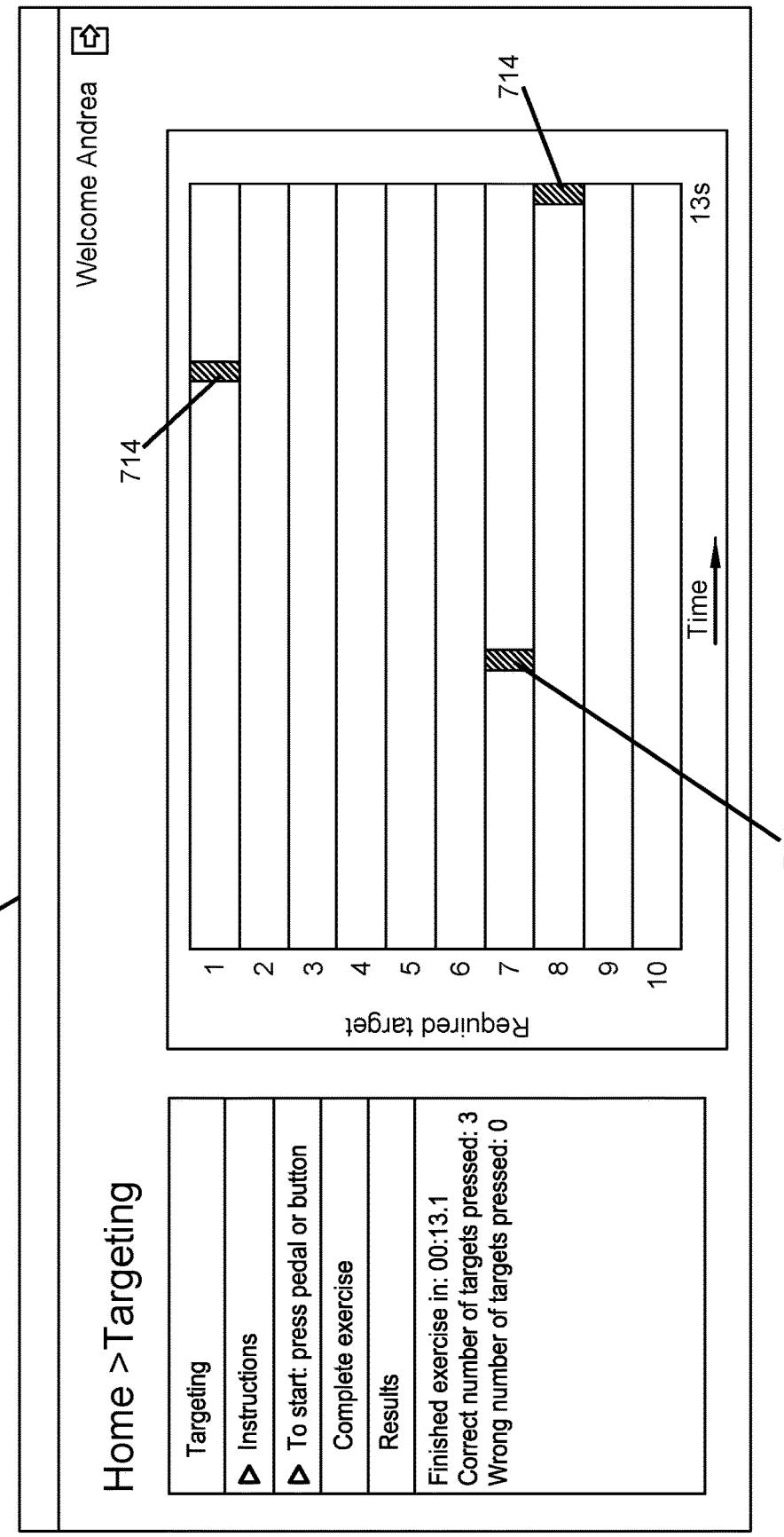
FIG. 22 is a view of another software page displayed during a targeting exercise.

Referring now to FIG. 22, when the targeting exercise is completed, the results are shown on a software page 712 opened on the monitor 402. The software page 712 may show the numbered targets 318 that were successfully pushed or touched over time. Colors may be used to show which numbered targets 318 were successfully touched. For example, an icon 714 having a color green may be used to indicate that a numbered target 318 was correctly touched in sequence, an icon 714 colored red and a number superimposed may be used to indicate that the wrong numbered target 318 was touched and which numbered target 318 was touched instead.

Polyp Removal Exercise

The polyp removal exercise can be performed using the simulator 120 fitted with the training box 600 and the hysteroscope 500 fitted with the forceps 530 (as, for example, depicted in FIG. 4B). The chamber 610 of the training box 600 simulates the uterine cavity of a female patient, and the objective of the polyp removal exercise is to cut or remove a synthetic polyp 622 from the chamber 610 within a predetermined time limit.

In some examples, the test taker has to successfully remove only one synthetic polyp 622 in order to complete the polyp removal exercise. In other examples, the test taker may have to successfully remove more than one synthetic polyp 622 in order to complete the polyp removal exercise. For example, the test taker may have to grasp and pluck multiple (e.g., ten) polyps using the forceps 530 equipped with the grasper 538, as depicted in FIG. 4D.

As described above, different types of chambers may be used for the polyp removal exercise. For example, the chambers may be equipped with only one synthetic polyp such as the chamber 610a (depicted in FIG. 18A) or the chamber 610b (depicted in FIG. 18B), which are both described in more detail above. In examples where the chambers are equipped with multiple synthetic polyps for exercises that require the test taker to grasp and pluck multiple (e.g., ten) polyps using the grasper 538, the synthetic polyps may be attached to the chambers by fasteners such as hook and loop fasteners, reusable adhesives, buttons, magnets and the like.

Depending on the parameters set by an administrator or proctor of the exercise, the test taker may or may not choose the type of chamber or synthetic polyp (e.g., 622a or 622b) used during the polyp removal exercise. When the chamber 610 including the synthetic polyp 622 is inserted into the training box 600, the polyp removal exercise may begin.

Figure 24:
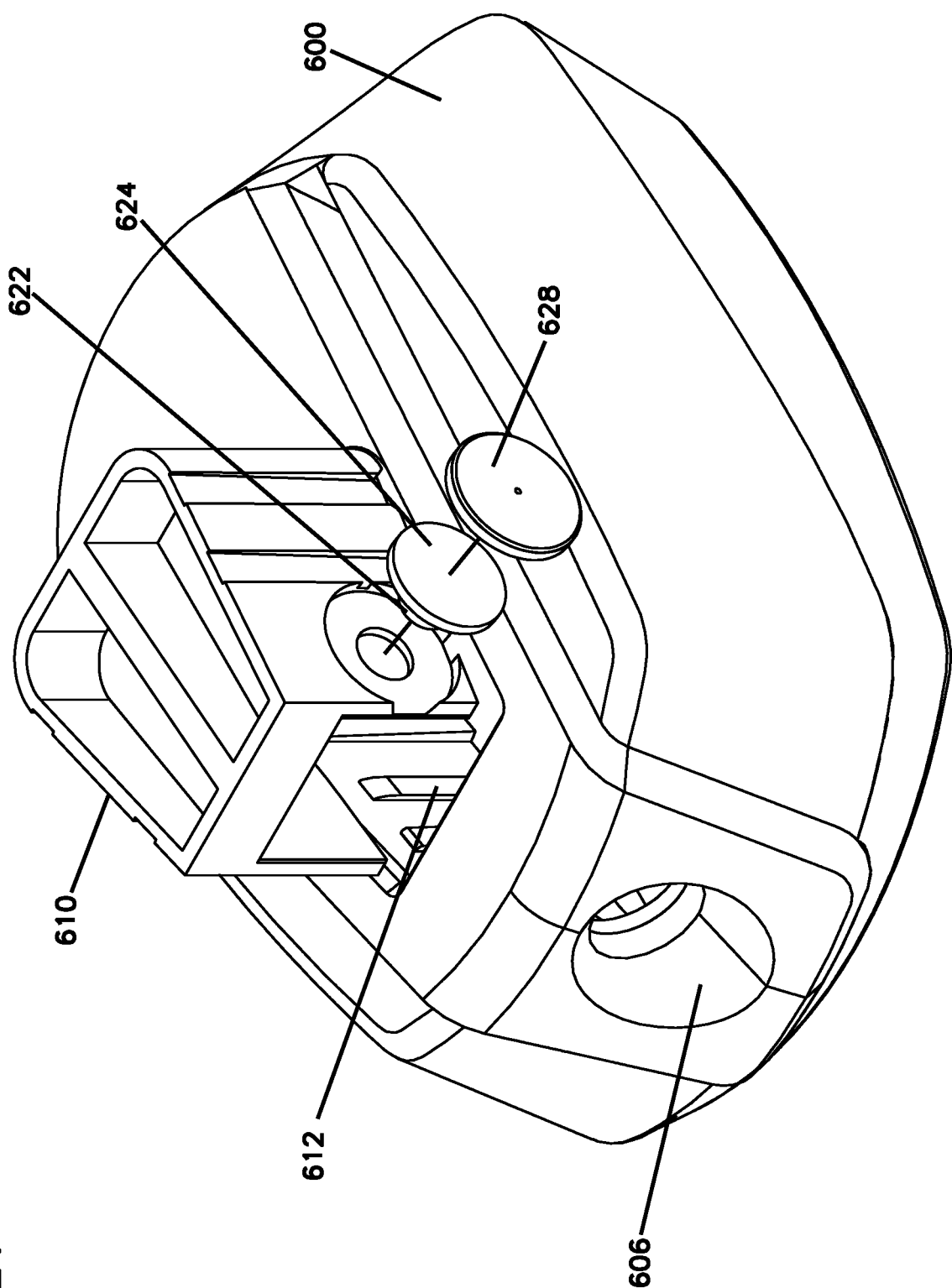
FIG. 24 is a perspective view of a set up for a training box before initiating a polyp removal exercise.

Referring now to FIG. 23, a software page 802 is opened on the monitor 402 for providing instructions 804 to the test taker for the polyp removal exercise. The instructions 804 may include initial steps for setting up the chamber 610 which may include the steps of placing one or more synthetic polyps 622 into the chamber 610, and inserting the chamber 610 with the synthetic polyp(s) 622 into the training box 600. An example set up for the chamber 610 is shown in FIG. 24. Additionally, the set up for the polyp removal exercise may include fitting the hysteroscope 500 with the forceps 530 (as depicted, for example, in FIG. 4B).

Figure 25:
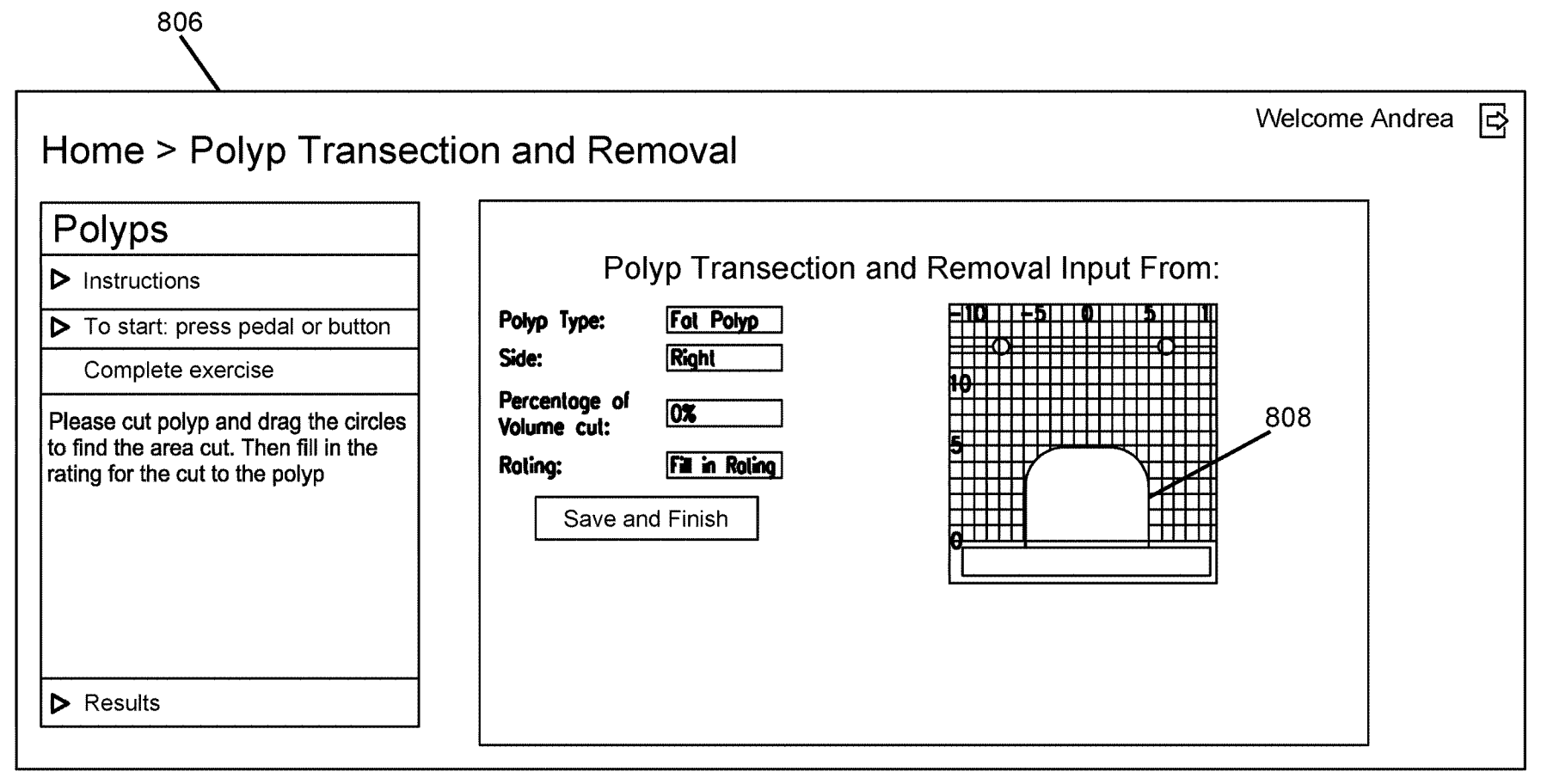

After the test taker presses the start button 212 or steps on the foot pedal 250, the polyp removal exercise begins. Referring now to FIG. 25, a new software page 806 is opened on the monitor 402. In some examples, the software page 806 may include an image 808 of a synthetic polyp 622 that is to be cut during the polyp removal exercise. In other examples, the software page 806 may include images of multiple synthetic polyps that need to be plucked and removed during the polyp removal exercise using the hysteroscope 500 fitted with the grasper 538.

During the polyp removal exercise, the test taker inserts the hysteroscope 500 into the opening 606 located on the front of the training box 600. The test taker may then look at the monitor 402 for viewing video images taken from the hysteroscope 500 inside the training box 600 for locating the one or more synthetic polyps 622 inside the chamber 610.

Once a synthetic polyp 622 is located, the test taker uses the forceps 530 to remove or cut the synthetic polyp 622 from the chamber 610. As described above, in some examples, the polyp removal exercise may require the test taker to remove multiple synthetic polyps using the forceps 530. In some examples, the chamber 610 is thereafter removed from the training box 600 and is replaced with a new chamber 610 for conducting further exercises using the training box 600.

Referring back to FIG. 19, in some examples, a synthetic polyp 622 that has been cut using the scissors 536 is removed from the chamber 610. Next, the cut synthetic polyp 622 while attached to the plate 624 is pushed into the polyp measuring station 650 for measuring the cut that was made on the synthetic polyp 622 during the polyp removal exercise.

Figure 26A:
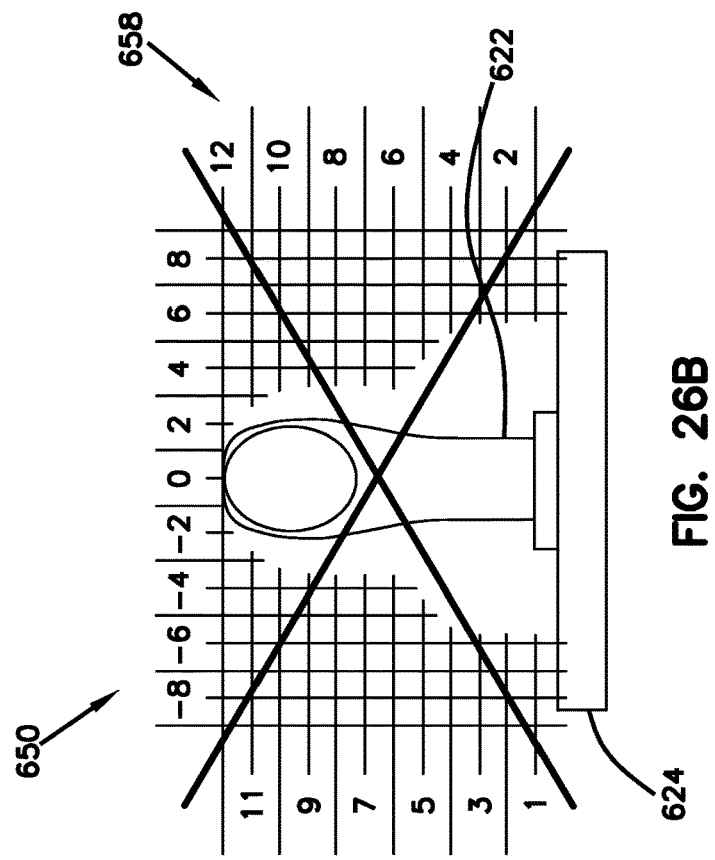
FIG. 26A is a view of a synthetic polyp correctly inserted in a polyp measuring station.
Figure 26B:
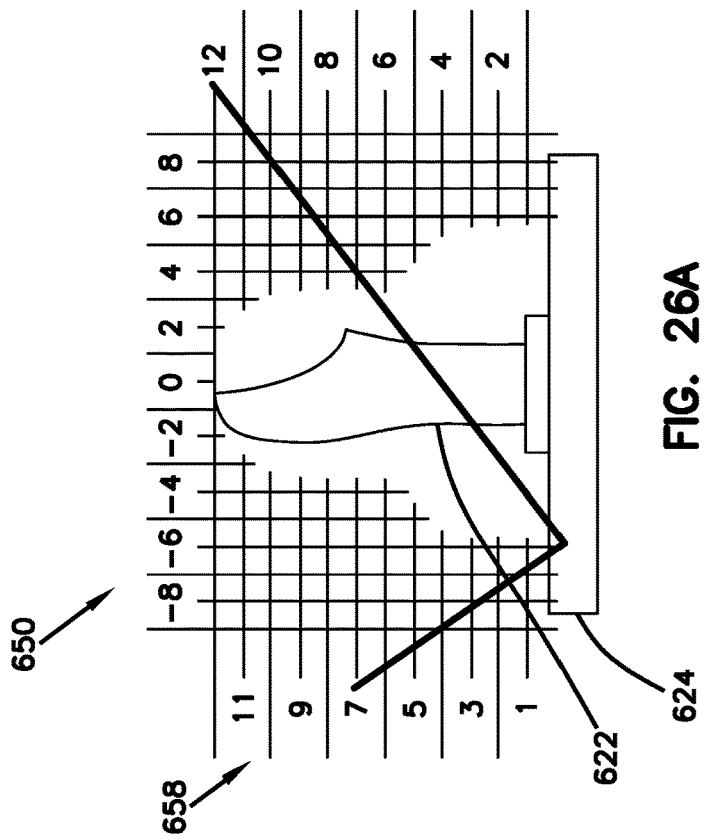
FIG. 26B is a view of a synthetic polyp incorrectly inserted in a polyp measuring station.

Referring now to FIG. 26A, the polyp measuring station 650 includes a grid and ruler 658 that can be used to measure the cut synthetic polyp 622. The cut synthetic polyp 622 should be inserted into the polyp measuring station 650 so that the cut is perpendicular to the front surface of the polyp measuring station 650. FIG. 26A shows the cut synthetic polyp 622 correctly inserted into the polyp measuring station 650, whereas FIG. 26B shows the cut synthetic polyp 622 incorrectly inserted into the polyp measuring station 650. The cut synthetic polyp 622 can be measured in the polyp measuring station 650 by recording where the cut starts and ends.

Figure 27:
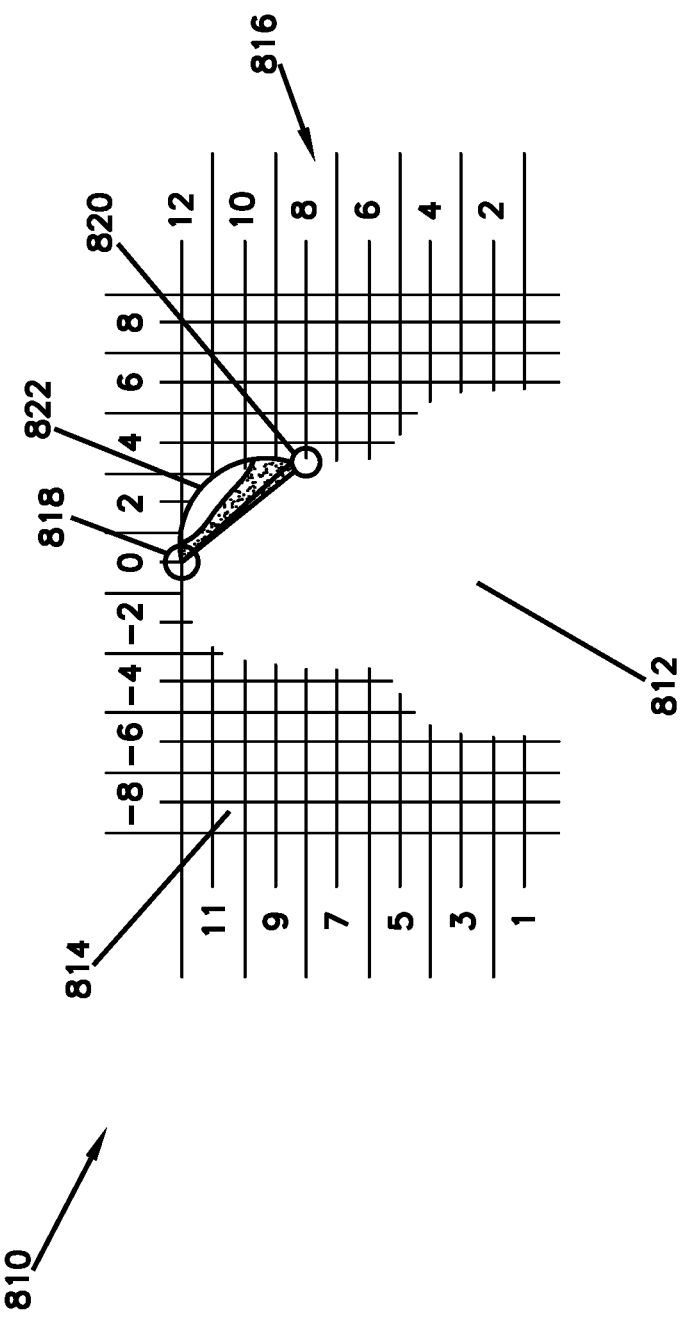
FIG. 27 is a view of a software page displayed during a polyp removal exercise.

Referring now to FIG. 27, the measurements from the polyp measuring station 650 can be entered into the software page 810. For example, the software page 810 may include an image 812 of the synthetic polyp overlapping a grid 814 having measurements 816 corresponding the ruler 658 in the polyp measuring station 650. The test taker or proctor can place an icon 818 onto the grid 814 representing where the cut begins and can place another icon 820 onto the grid 814 representing where the cut ends. The software page 810 may then highlight an area 822 of the image 812 of the synthetic polyp which represents the area that was cut and removed from the synthetic polyp 622 during the polyp removal exercise.

Figure 28:
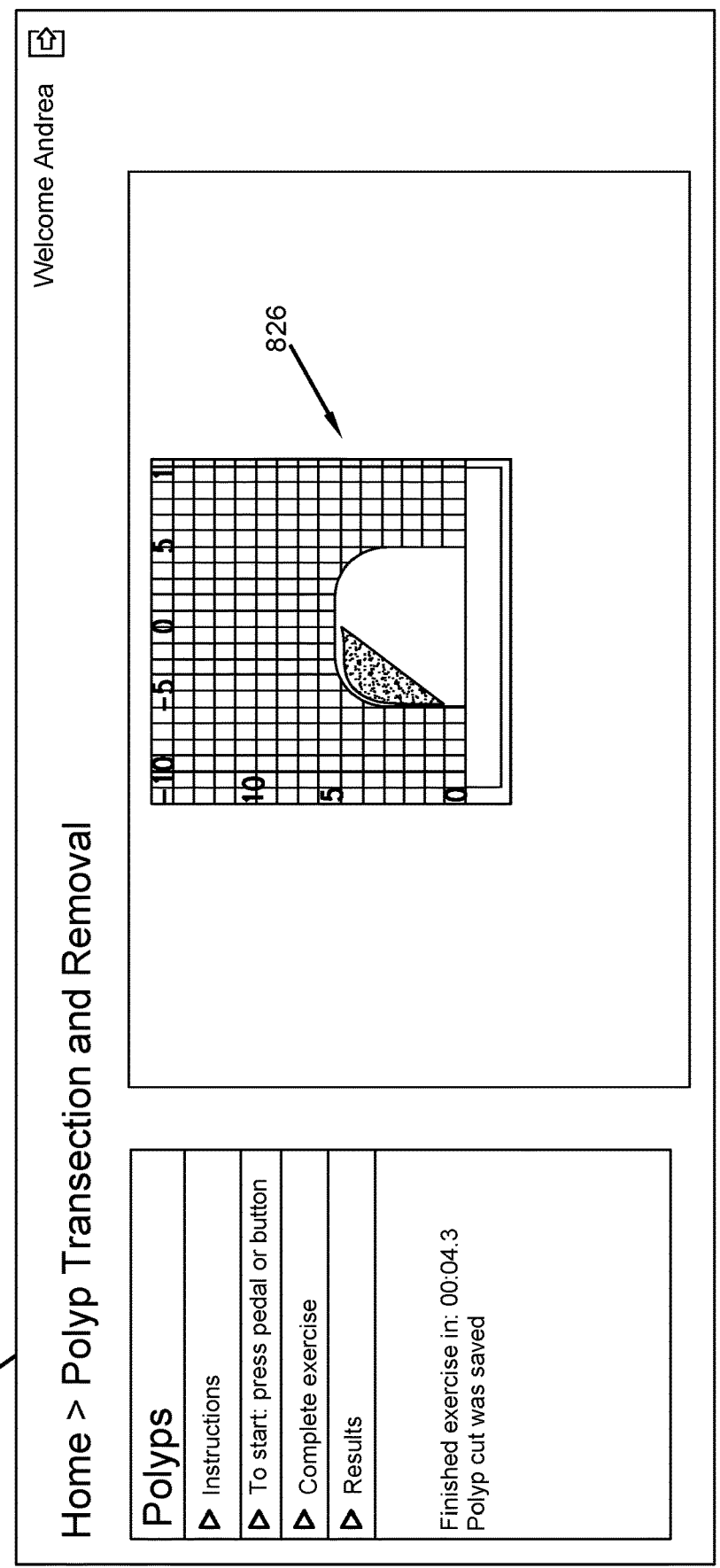
FIG. 28 is a view of another software page displayed during a polyp removal exercise.

Referring now to FIG. 28, the data on the cut synthetic polyp 622 can be saved and a summary of the results 826 can be given on a new software page 824. Afterwards, the chamber 610 can be replaced with a new chamber 610 having an uncut synthetic polyp 622 so that the polyp removal exercise may begin for another test taker or the same test taker.

The various embodiments described above are provided by way of illustration only and should not be construed to limit the claims attached hereto. Those skilled in the art will readily recognize various modifications and changes that may be made without following the example embodiments and application illustrated and described herein, and without departing from the true spirit and scope of the following claims.

What is claimed is:

1. A system for simulating a medical procedure, the system comprising:
    a base station connected to a computer and monitor;
    a training box connected to the base station, the training box including a housing having a chamber positioned therein, the chamber being adapted to simulate the shape of a uterine cavity and includes an opening for receiving an instrument configured to perform medical training and evaluation exercises inside the chamber; wherein the chamber includes one or more synthetic polyps adapted to be removed or cut by the instrument; and
    a polyp measuring station configured to measure a cut on a synthetic polyp.

2. The system of claim 1, wherein the chamber includes switches adapted to detect whether one or more numbered targets have been touched by the instrument.

3. The system of claim 2, wherein the switches are electro-mechanical switches and the instrument is a targeting probe.

4. The system of claim 2, wherein the monitor includes a screen having icons representing the one or more numbered targets inside the chamber.

5. The system of claim 2, wherein the instrument includes a camera for capturing video images, and the monitor displays the video images inside the chamber from the instrument.

6. The system of claim 1, wherein the chamber is adapted to be removed from the training box and is replaceable with another chamber.

7. The system of claim 1, wherein the one or more synthetic polyps in the chamber are replaceable with other synthetic polyps.

8. A method for simulating a hysteroscopy procedure, the method comprising:
    providing a base station adapted to communicate with a computer having a monitor, and a training box connected to the base station, the training box includes a housing having a chamber adapted to simulate the shape of a uterine cavity and having one or more numbered targets inside;
    prompting a test taker to touch a first numbered target inside the chamber using an instrument;
    detecting whether the test taker has touched the first numbered target;

prompting the test taker to touch additional numbered targets using the instrument according to a predefined sequence of number targets;

detecting whether the test taker has touched the additional numbered targets according to the predefined sequence of number targets; and displaying the results on the monitor.

9. The method of claim 8, further comprising displaying on the monitor a screen having icons representing the one or more numbered targets inside the chamber.

10. The method of claim 9, further comprising changing an icon to have a first color when an associated numbered target is touched according to the predefined sequence.

11. The method of claim 10, further comprising changing an icon to have a second color when an associated numbered target is touched outside the predefined sequence.

12. The method of claim 9, further comprising displaying video images captured from the instrument on the monitor.

13. The method of claim 8, wherein the results include icons representing the numbered targets that were touched by the instrument over time.

14. A method for simulating a hysteroscopy procedure, the method comprising:

providing a base station adapted to communicate with a computer having a monitor, a training box connected to the base station, the training box including a housing having a chamber adapted to simulate the shape of a uterine cavity and having a synthetic polyp;

prompting a test taker to use an instrument to cut the synthetic polyp;

prompting the test taker to remove the synthetic polyp from the chamber;

prompting the test taker to insert the synthetic polyp into a polyp measuring station to measure where a cut on the synthetic polyp starts and ends;

displaying an image of a synthetic polyp overlapping a grid;

receiving a first icon on the grid representing where the cut begins;

receiving a second icon on the grid representing where the cut ends; and highlighting an area of the image of the synthetic polyp representing an area that was cut and removed from the synthetic polyp.

15. The method of claim 14, further comprising prompting the test taker to remove the chamber from the training box and insert a new chamber into the training box.

16. The method of claim 14, further comprising prompting the test taker to remove a synthetic polyp from the chamber and insert a new synthetic polyp into the chamber.

* * * * *